US008945042B2

(12) United States Patent
Lee et al.

(10) Patent No.: US 8,945,042 B2
(45) Date of Patent: Feb. 3, 2015

(54) MEDICAL FLUID MACHINE WITH SUPPLY AUTOCONNECTION

(71) Applicants: Baxter International Inc., Deerfield, IL (US); Baxter Healthcare S.A., Glattpark (Opfikon) (CH)

(72) Inventors: Patrick Lee, Long Grove, IL (US); John Biewer, Palm Harbor, FL (US); Robert W. Childers, Trinity, FL (US); Mark W. Foohey, Austin, TX (US); Richard R. Gilbert, II, Clearwater, FL (US); Andrey Kopychev, Clearwater, FL (US); Randy Murphey, Pleasant Prairie, WI (US); Austin J. Orand, Austin, TX (US); Douglas Reitz, Green Oaks, IL (US); Rodolfo Roger, Clearwater, FL (US); John E. Steck, Round Lake, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 13/750,713

(22) Filed: Jan. 25, 2013

(65) Prior Publication Data
US 2013/0138037 A1 May 30, 2013

Related U.S. Application Data

(63) Continuation of application No. 13/153,033, filed on Jun. 3, 2011, now Pat. No. 8,361,009, which is a continuation of application No. 11/773,523, filed on Jul. 5, 2007, now Pat. No. 7,955,295.

(51) Int. Cl.
*A61M 1/00* (2006.01)
*A61M 39/00* (2006.01)
(Continued)

(52) U.S. Cl.
USPC ............................ 604/29; 604/533; 417/477.2

(58) Field of Classification Search
USPC .................... 604/29, 533–538; 138/69, 96 R; 417/477.2
See application file for complete search history.

(56) References Cited

U.S. PATENT DOCUMENTS

| 4,405,315 A | 9/1983 | Handt |
|---|---|---|
| 4,439,188 A | 3/1984 | Dennehey et al. |

(Continued)

FOREIGN PATENT DOCUMENTS

| DE | 202005016276 | 12/2005 |
|---|---|---|
| EP | 1279409 | 1/2003 |

(Continued)

OTHER PUBLICATIONS

International Search Report and Written Opinion for International Application No. PCT/US2008/068959 mailed on Jan. 5, 2010.

(Continued)

*Primary Examiner* — Kevin C Sirmons
*Assistant Examiner* — Andrew Gilbert
(74) *Attorney, Agent, or Firm* — K&L Gates LLP

(57) ABSTRACT

A medical fluid system including: fluid containers and a tube extending from same, each tube including a cap; a pumping cassette including port spikes; a medical fluid machine including: occluders; a shuttle configured to receive the tubes, wherein each tube is associated with one of the occluders; a driving mechanism translating the shuttle; a cap removal device between the cassette and the shuttle; and a control unit programmed to cause: (i) the occluders to pinch their tubes, (ii) cause the driving mechanism to translate the shuttle towards the fluid pumping cassette, the cap removal device engaging the tube caps, (iii) the driving mechanism to translate the shuttle away from the fluid pumping cassette and cap removal device, pulling the tube caps off of the tubes, and (iv) the driving mechanism to translate the shuttle back towards the fluid pumping cassette for the port spikes to spike the occluded tubes.

20 Claims, 22 Drawing Sheets

(51) Int. Cl.
  *A61M 39/10* (2006.01)
  *F04B 43/08* (2006.01)
  *F04B 43/12* (2006.01)
  *F04B 43/06* (2006.01)

(56) References Cited

U.S. PATENT DOCUMENTS

| | | | |
|---|---|---|---|
| 4,464,336 A | | 8/1984 | Hiramoto |
| 4,475,900 A | | 10/1984 | Popovich et al. |
| 4,655,753 A | | 4/1987 | Bellotti et al. |
| 4,882,496 A | | 11/1989 | Bellotti et al. |
| 4,895,570 A | | 1/1990 | Larkin |
| 5,047,011 A | * | 9/1991 | Caron et al. ............ 604/29 |
| 5,088,515 A | | 2/1992 | Kamen |
| 5,178,182 A | | 1/1993 | Kamen |
| 5,221,267 A | | 6/1993 | Folden |
| 5,350,357 A | * | 9/1994 | Kamen et al. ............ 604/29 |
| 5,611,506 A | | 3/1997 | Berger et al. |
| 5,989,423 A | | 11/1999 | Kamen |
| 6,234,538 B1 | | 5/2001 | Lauer |
| 6,293,921 B1 | * | 9/2001 | Shinmoto et al. ............ 604/29 |
| 6,468,424 B1 | * | 10/2002 | Donig et al. ............ 210/232 |
| 6,743,201 B1 | | 6/2004 | Donig et al. |
| 6,913,056 B2 | | 7/2005 | Landherr et al. |
| 7,115,228 B2 | | 10/2006 | Lundtveit et al. |
| 7,727,220 B2 | * | 6/2010 | Wieslander et al. .......... 604/411 |
| 7,736,328 B2 | | 6/2010 | Childers et al. |
| 7,766,301 B2 | | 8/2010 | Gray et al. |
| 7,955,295 B2 | * | 6/2011 | Lee et al. ............ 604/29 |
| 8,361,009 B2 | * | 1/2013 | Lee et al. ............ 604/29 |
| 8,512,275 B2 | * | 8/2013 | Childers et al. ............ 604/29 |
| 2003/0141009 A1 | | 7/2003 | Landherr et al. |

FOREIGN PATENT DOCUMENTS

| | | |
|---|---|---|
| JP | 2001-037874 | 2/2001 |
| JP | 2003-052813 | 2/2003 |
| JP | 2006-225150 | 8/2006 |

OTHER PUBLICATIONS

PCT/US2008/068959 International Search Report, received on Dec. 1, 2008.
Communication from European Patent Office for European Patent Application No. 08781256.6 received on Aug. 2, 2012.
Mexican Office Action for Patent Application No. MX/a/2010/000288 dated Aug. 15, 2012.
Japanese Patent Application No. 2011-147666, Mailing Date Feb. 15, 2013 (translation).
Japanese Office Action issued Sep. 3, 2013 in corresponding Japanese Patent Application No. 2010-515244.

* cited by examiner

MEDICAL FLUID MACHINE WITH SUPPLY AUTOCONNECTION

PRIORITY CLAIM

This application claims priority to and the benefit as a continuation application of U.S. Pat. No. 8,361,009 filed Jun. 3, 2011, which is a continuation of U.S. Pat. No. 7,955,295, filed Jul. 5, 2007, entitled, "Fluid Delivery System With Autoconnect Features", the entire contents of which are incorporated herein by reference and relied upon.

BACKGROUND

In general, the present disclosure relates to medical fluid delivery systems that employ a disposable cassette. In particular, the present disclosure provides systems and methods for cassette-based dialysis medical fluid therapies, including but not limited to those using peristaltic pumps and diaphragm pumps.

Due to various causes, a person's renal system can fail. Renal failure produces several physiological derangements. The balance of water, minerals and the excretion of daily metabolic load is no longer possible and toxic end products of nitrogen metabolism (urea, creatinine, uric acid, and others) can accumulate in blood and tissue. Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving.

Hemodialysis and peritoneal dialysis are two types of dialysis therapies used commonly to treat loss of kidney function. Hemodialysis treatment utilizes the patient's blood to remove waste, toxins and excess water from the patient. The patient is connected to a hemodialysis machine and the patient's blood is pumped through the machine. Catheters are inserted into the patient's veins and arteries so that blood can flow to and from the hemodialysis machine. The blood passes through a dialyzer of the machine, which removes waste, toxins and excess water from the blood. The cleaned blood is returned to the patient. A large amount of dialysate, for example about 120 liters, is consumed to dialyze the blood during a single hemodialysis therapy. Hemodialysis treatment lasts several hours and is generally performed in a treatment center about three or four times per week.

Peritoneal dialysis uses a dialysis solution, or "dialysate," which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow APD and continuous flow peritoneal dialysis ("CFPD"). CAPD is a manual dialysis treatment. The patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity, and allow the transfer of waste, toxins and excess water to take place. The source can be multiple sterile dialysate solution bags.

APD machines pump spent dialysate from the peritoneal cavity, though the catheter, to the drain. As with the manual process, several drain, fill and dwell cycles occur during APD. A "last fill" occurs at the end of CAPD and APD, which remains in the peritoneal cavity of the patient until the next treatment. Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, systems clean or regenerate spent dialysate instead of discarding it. The systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroduction of the dialysate into the peritoneal cavity. Additional sensors are employed to monitor the removal of ammonia. CFPD systems are typically more complicated than batch systems.

Hemodialysis, APD (including tidal flow) and CFPD systems can employ a pumping cassette. The pumping cassette typically includes a flexible membrane that is moved mechanically to push and pull dialysis fluid out of and into, respectively, the cassette. Certain known systems include flexible sheeting on one side of the cassette, while others include sheeting on both sides of the cassette. Positive and/or negative pressure can be used to operate the pumping cassettes. Cassettes with other pumps or fluid transfer mechanisms may be used.

There are two concerns for patient using dialysis treatments, especially for home-use peritoneal dialysis. Dialysis patients tend to be elderly, with many aged 50 or 60 years, and older. Connecting bags of dialysis fluid to a treatment machine may be difficult because of the force required to push a connecting spike through a sealing membrane. This force can be as much as 20 lbs or more, and may be required to connect each of four bags every night. The force and physical dexterity required make it difficult for significant numbers of patients to make the connections properly, e.g., without spiking through a connecting line, rather than a sealing membrane. The difficulty encountered in making connections may lead to improper touching and contamination of one or more of the lines, if the patient inadvertently grasps or touches a connector or an portion which is sterile and is intended to remain sterile. Inadvertent touches can lead to infections and peritonitis, and may require hospitalization or other stressful procedures.

Accordingly, what is needed is a better way to connect containers of dialysis solutions to a dialysis machine, such as a peritoneal dialysis machine. The present disclosure addresses the above-described needs and concerns.

SUMMARY

A first embodiment is a system for automatically connecting tubing while maintaining sterility. The system includes a frame for mounting adjacent a cassette in a dialysis machine, a shuttle mounted within the frame, the shuttle configured for receiving tubing from at least two containers, the tubing including a cap, a shuttle driving system for translating the shuttle within the frame, and at least two rotating fingers configured for receiving and removing the caps, the fingers mounted to the frame and operably adjacent the shuttle. The system also includes a finger rotating system configured for rotating the fingers in a plane parallel to a direction of travel of the shuttle, and a control system for operating the system for automatically connecting tubing, wherein the system for automatically connecting tubing is configured for receiving sterile tubing from at least two containers, the fingers are configured for receiving caps from the tubing, the shuttle is configured for advancing the ends of the tubing, the control system is configured to rotate the fingers to remove the caps, and the cassette comprises at least two spikes for piercing sterile sealing membranes of the tubing and making a sterile connection.

Another embodiment is a system for automatically connecting sterile tubing. The system includes a frame for mounting adjacent a cassette in a dialysis machine, a shuttle mounted within the frame, the shuttle including a tubing side and a cassette side, the shuttle configured for receiving tubing from a plurality of sterile containers of dialysis fluid, each container including a length of tubing and a cap, a shuttle driving system for translating the shuttle within the frame, and a plurality of rotating fingers, each rotating finger configured for receiving and removing the cap from the length of tubing and configured for receiving and removing a cassette port cap, the rotating fingers mounted to the frame and adjacent the shuttle. The system also includes a finger rotating system including a shaft configured for rotating the fingers in a plane parallel to a direction of travel of the shuttle, and a control system for operating the system for automatically connecting tubing, wherein the system for automatically connecting tubing is configured for receiving tubing of a plurality of containers of dialysis fluid, the fingers configured for receiving caps from the tubing and cassette port caps, and the control system configured to translate the shuttle, to rotate the fingers, and to advance ends of the tubing into an adjacent cassette, the cassette including at least two spikes for piercing sealing membranes of the tubing and making a sterile connection.

Another embodiment is a system for automatically connecting tubing. The system includes a frame for mounting adjacent a dispensing machine, a shuttle mounted within the frame, the shuttle including a tubing side and a dispensing side, the shuttle configured for receiving tubing from a plurality of containers, and a shuttle driving system for translating the shuttle within the frame. The system also includes a plurality of rotating fingers, each rotating finger configured for receiving and removing a tubing cap and also configured for receiving and removing a dispensing machine port cap, the rotating fingers mounted to the frame and adjacent the shuttle, a finger rotating system including a shaft configured for rotating the fingers in a plane parallel to a direction of travel of the shuttle, and a control system for operating the system for automatically connecting tubing, wherein the system for automatically connecting tubing is configured for receiving tubing of a plurality of containers of liquid, the fingers configured for receiving tubing caps and dispensing machine port caps, and the control system is configured to translate the shuttle, to rotate the fingers, and to advance ends of the tubing into an adjacent dispensing machine, the dispensing machine including at least two spikes for piercing sealing membranes of the tubing.

Another embodiment is a system for automatically connecting tubing. The system includes a frame for mounting adjacent a dispensing machine, a platform mounted within the frame, the platform including a tubing side and a dispensing side, the platform configured for receiving tubing from a plurality of containers, and a plurality of moving mounts on the platform, each mount further including a driving system for advancing and retracting the mount. The system also includes a plurality of rotating fingers, each rotating finger configured for receiving and removing a tubing cap and also configured for receiving and removing a dispensing machine port cap, the rotating fingers mounted to the frame and adjacent the platform, a finger rotating system including a shaft configured for rotating the fingers in a plane parallel to a direction of travel of the mounts, and a control system for operating the system for automatically connecting tubing, wherein the system for automatically connecting tubing is configured for receiving tubing from a plurality of containers of liquid, the fingers are configured for receiving tubing caps and dispensing machine port caps, and the control system is configured to translate the mounts individually, to rotate the fingers, and to advance ends of the tubing into an adjacent dispensing machine, the dispensing machine including at least two spikes for piercing sealing membranes of the tubing.

Another embodiment is a method for connecting dialysis bags to a dialysis cassette. The method includes placing tubing from a dialysis bag into a shuttle of an autoconnect machine, the autoconnect machine including a frame, a shuttle and shuttle driving system mounted on the frame, a plurality of rotating fingers, each finger configured for receiving a cap from dialysis bag tubing, and a finger rotating system for rotating the fingers, and wherein the tubing fits into tubing runs atop the shuttle, placing the tubing cap into a first pocket of one of the rotating fingers of the autoconnect machine, causing the rotating finger with the tubing cap to rotate in a direction away from the shuttle and toward a disposable cassette on an opposite side of the rotating fingers. The method also includes steps of translating the shuttle a distance in a direction toward the disposable cassette, wherein translating the shuttle rotates or translates the rotating finger with the tubing cap, and causes only the rotating finger into which the tubing cap was placed to capture a port cap from a port of the disposable cassette in a second pocket of the rotating finger, translating the shuttle in a direction away from the cassette, removing the tubing cap from the dialysis bag and leaving the tubing cap in the first pocket, rotating the rotating fingers in a direction toward the shuttle, removing the port cap from the port of the dialysis cassette and leaving the port cap in the second pocket, and translating the shuttle toward the dialysis cassette and causing a spike in the port of the disposable cassette to pierce a sealing membrane in the tubing, and translating the occluder to allow dialysis fluid to flow in the tubing.

Another embodiment is a method for connecting fluid containers. The method includes placing a connector from a fluid container into an autoconnect machine, placing a tubing cap from one of the fluid containers into a pocket of one of a plurality of fingers of the autoconnect machine, causing the finger to move or rotate in a direction toward a dispensing machine on a different side of the fingers. The method also includes steps of translating the tubing and the tubing cap a distance in a direction toward the dispensing machine, wherein translating rotates the plurality of fingers, and causes only the finger into which the tubing cap was placed to capture a port cap from a port of the dispensing machine, translating the tubing in a direction away from the dispensing machine, removing the tubing cap from the tubing and leaving the tubing cap from the tubing in the pocket, rotating the fingers away from the dispensing machine and in a direction to remove the port cap from the port of the dispensing machine, and translating the tubing toward the dispensing machine and causing a spike in the port of the dispensing machine to pierce a sealing membrane in the tubing.

As will be clear from the disclosure below, an autoconnect device may be used for both peritoneal dialysis and hemodialysis. In addition, embodiments of an autoconnect device may be used for dispensation or administration of other fluids with devices other than dialysis or hemodialysis machines, such as for blood or blood-substitute transfusions. Additional features and advantages of the present disclosure are described in, and will be apparent from, the following Detailed Description of the Disclosure and the figures.

DETAILED DESCRIPTION

Figure 1:
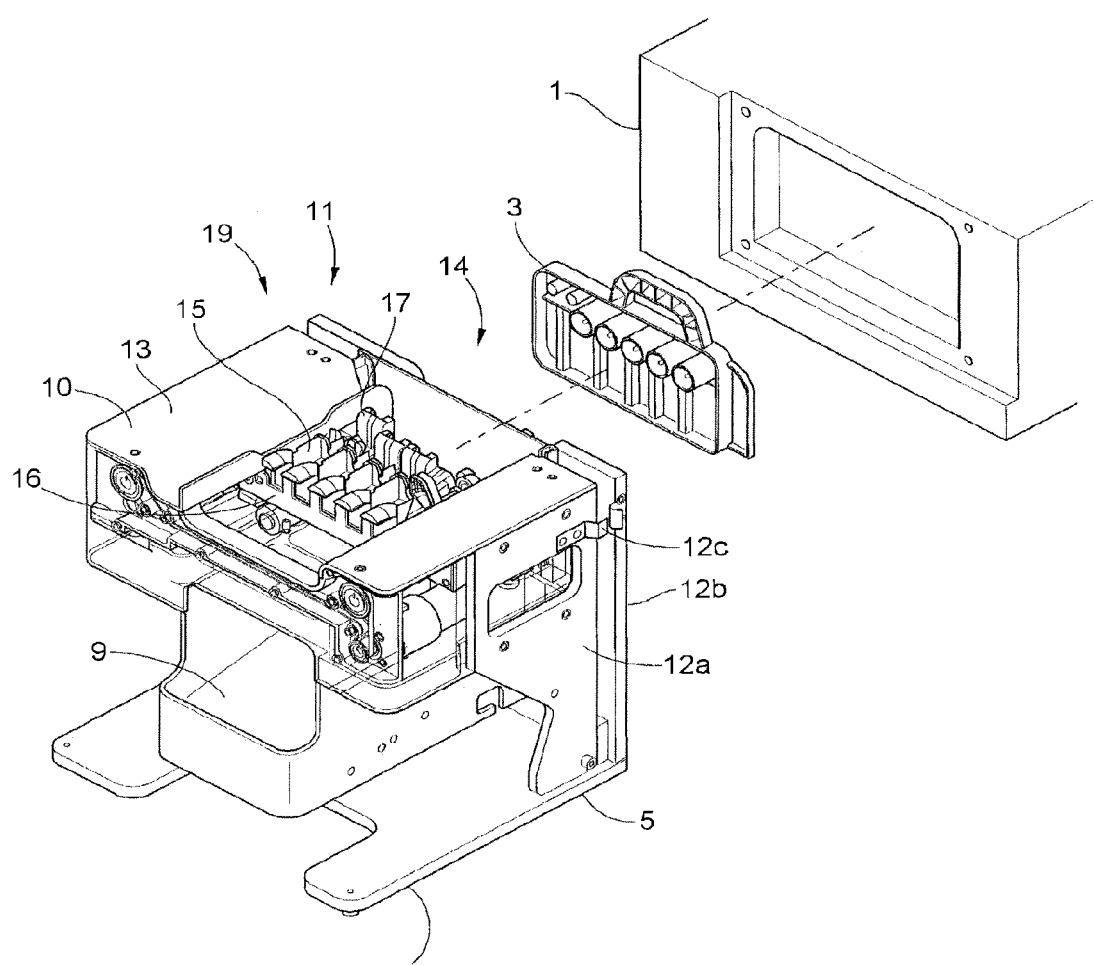
FIG. 1 is an exploded view of a first embodiment of an autoconnect mechanism used with a disposable cassette and a dialysis machine.

The present disclosure relates to medical fluid delivery systems that employ a pump, such as a diaphragm pump or a peristaltic pump. In particular, the present disclosure provides systems, methods and apparatuses for cassette-based dialysis therapies including but not limited to hemodialysis, hemofiltration, hemodiafiltration, any type of continuous renal replacement therapy ("CRRT"), congestive heart failure treatment, CAPD, APD (including tidal modalities) and CFPD. The cassette is disposable and typically discarded after a single use or therapy, reducing risks associated with contamination. The autoconnect device is intended for reuse as a part of the dialysis machine.

Patient Care

An autoconnect device, as discussed below, is intended to ease the burden on dialysis patients, who may be elderly and in poor health, and those who care for them, who may also be elderly, and who may also be in poor health. The daily task of hooking up dialysis fluid bags is indeed difficult for those with limited strength. In addition, it is easy to inadvertently break sterility or to contaminate the instrument or the container of fluid. In general terms, and for which a detailed explanation is given below, the autoconnect device works in the following manner.

After the cassette is loaded into the dialysis machine, the user attaches tubing from one or more dialysis bags by laying tubing in the top portion of the device and by placing caps from the tubing in the tops of special fingers on the top of the device. The autoconnect machine is then activated. A series of pinchers or occluders grasps the tubing and a shuttle then moves the tubing forward with the shuttle. The forward movement also causes the fingers to rotate forward, in the direction of the shuttle motion and toward the dialysis disposable cassette. Only those fingers with a tubing cap will rotate sufficiently to contact a shielding cap from a port of the dialysis disposable cassette. These fingers are rotated into the shielding cap or caps and grasp the cap or caps. After this forward rotation, the shuttle reverses direction, and the cap from the tubing, held in place by a restraining orifice atop the finger, is removed by remaining stationary while the shuttle and the tubing moves backward. The finger is now rotated in the opposite direction, while grasping the cap from the disposable cassette port, the rotation causing the cassette port cap to remain in the top of the rotating finger, thus removing the port cap. Both caps have now been removed without the user touching the caps.

The top of the finger (or fingers) now contains a cap from the tubing and a cap from the cassette port. The fingers are then rotated downward, causing the caps to fall from the tops of the fingers into a chute, drawer, or other area. The fingers remain in the downward position while therapy is in progress. Once the caps are disposed of, the shuttle again reverses direction. At this point, the caps have been removed and all that remains before dialysis is to connect the end of the tubing, with its sterile seal, to the cassette port, which is also sterile. The shuttle now translates forward pushing on the connector while the tubing is held in place by the occluder, and extends the tubing into a piercing needle contained within the cassette port. The piercing needle is preferably somewhat recessed from the outer lip of the port for ease of maintaining the sterile environment and a sterile connection. Once the needle pierces the membrane seal of the dialysis tubing, the connection is made and will remain secure. With the dialysis containers now attached via a sterile connection, an after the occluder is released, dialysis may now begin. In the embodiments discussed below, the autoconnect device may be used to connect from one to five containers of dialysis fluid. Other embodiments may be used to connect less than five or more than five containers. Still other embodiments may be used for one or more fluid containers other than dialysis fluid, such as blood, blood substitutes, saline solution, nutritional fluids, medications, and others. For example, one of the containers may include a neutral fluid, such as saline, and a medication needed by the patient, such as heparin, insulin, or an antibiotic. These medication fluids may just as easily be used with the autoconnect device and a device for downstream infusion or dispensing.

The Autoconnect Device

Referring now to the drawings and in particular to FIG. 1, a dialysis machine 1 is intended for use with a disposable dialysis cassette 3 and an autoconnect machine 5. Autoconnect machine 5 in this embodiment includes a frame or base 7, a central area 9 for disposal of caps from the dialysis cassette and from bags of dialysis fluid. In this embodiment, frame 7 includes sides 12a and back portions 12b, joined by hinges 12c. Main chassis 10 includes a central area 11 includes discrete portions of channels 14 for tubing from the dialysis bags. Autoconnect 5 also includes top covers 13 on either side to shield and protect the inner workings. Also included in top working area 19 is a shuttle 15 for advancing the tubing, an occluder 16, and fingers 17 for removing caps from the dialysate bags and from the dialysis cassette.

Figure 3A:
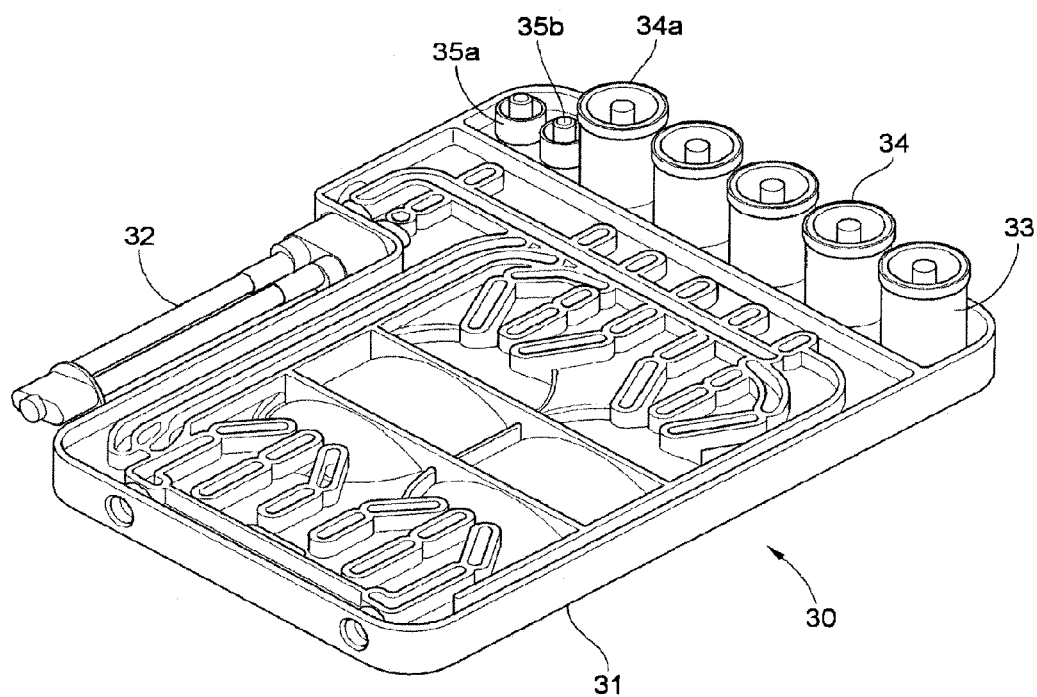
FIGS. 3A and 3B are isometric views of alternate embodiments of disposable cassettes for use with an autoconnect mechanism and a dialysis machine.

In using the autoconnect device, a plurality of containers of dialysis fluid may be positioned in the vicinity of the dialysis machine or near the autoconnect device. Since dialysis bags typically include tubing about 2 feet long, either position is possible and may be suitable. If the dialysis machine includes one or more facilities for heating, the containers of dialysis fluid are desirable heated to a temperature close to body temperature before use. Alternatively, the disposable dialysis cassette may include provisions for heating dialysis fluid as it is being pumped. For example, the dialysis cassette 30 depicted in FIG. 3A may be used to warm the dialysis fluid.

Figure 2:
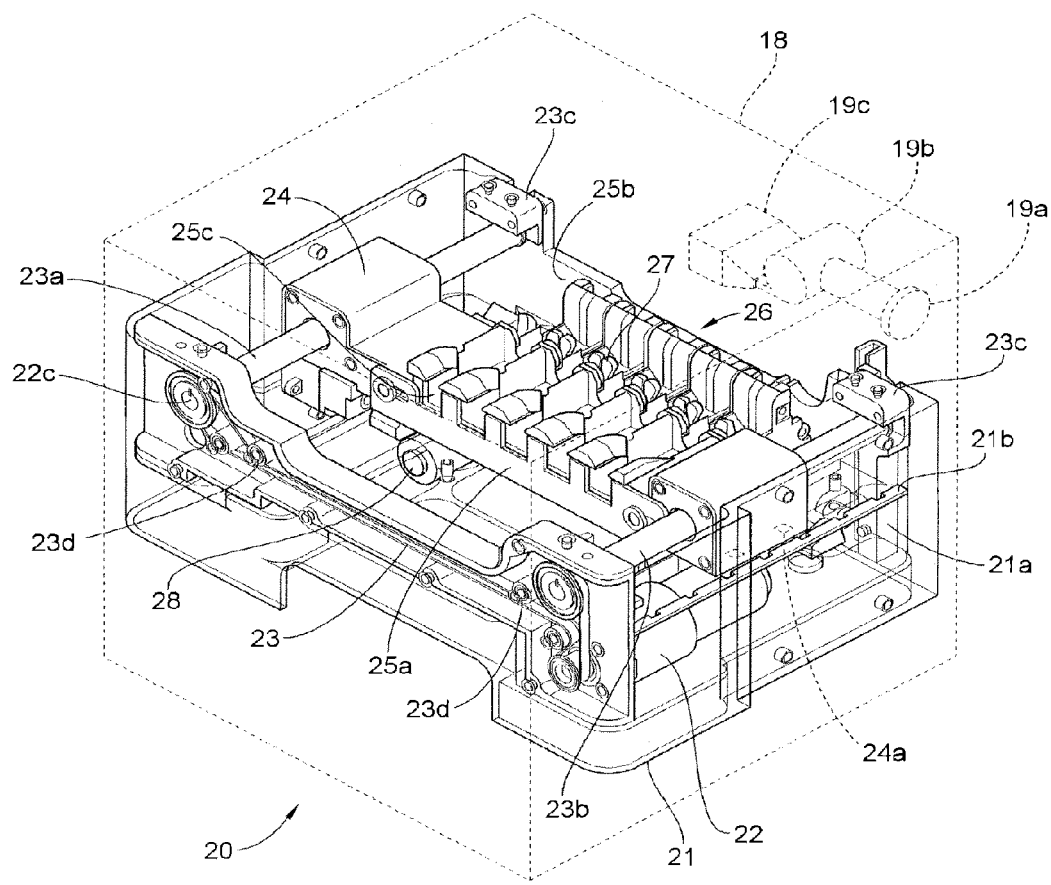
FIG. 2 is an isometric view of a second embodiment of an autoconnect mechanism for use with a dispensing machine.

The embodiment of FIG. 1 may be used as presented for automatically connecting containers of dialysis fluid to the pumping cassette while preserving a sterile connection. Alternatively, the main chassis portion may be used separately, as shown in FIG. 2, as an autoconnect device 20. Autoconnect 20 includes a frame 21, frame back wall 21a, and also includes a drive motor 22 and a drive system 23 for positioning shuttle 24. Drive system 23 includes left and right lead screws 23a, 23b, and a power transmission system as shown, including a timing belt, and belt tensioners as needed, to distribute power from motor 22 to the two lead screws. The system could use gears rather than a timing belt. Drive system 23 includes at least mounts 23c and bearings 23d as shown, and also preferably includes a drive train and any necessary gear reduction for matching motor 22 to the desired speed for advancing and retracting shuttle 24. A brushed 24 VDC planetary gear motor, with a suitable controller, has been found satisfactory for the motor for this application. Other suitable motors may be used.

Autoconnect 20 includes a central area 26 with discrete channels for tubing from dialysis containers, and also includes front occluder 25a and a rear occluder 25b for occluding or pinching tubing from the dialysis containers. In this embodiment, central area 26 includes five channels for placement of tubing from five dialysis containers. Occluders 25a, 25b each include openings for the tubing, in this case five openings 25c. In one embodiment, occluders 25a, 25b are both part of a single, U-shaped piece of sheet metal, in which occluder 25a performs the occlusion function, i.e., pinching the tubing so no flow is possible, while occluder 25b acts only to secure the membrane port into shuttle 24. When the occluder is actuated and no flow is possible in the tubing, there will be no premature flow of fluid during spiking, and the machine may, with confidence, perform an integrity test. There are also five fingers 27 for grasping and removing caps from the ends of the dialysis tubing, and also for grasping and removing caps from the ports of a dialysis cassette used with the autoconnect and a dialysis machine. Visible also in FIG. 2 is a motor 28 for rotating fingers 27. A brushed 24 VDC planetary gear motor, with a suitable controller, has also been found satisfactory for this application. Other suitable motors may be used.

Autoconnect device 20 preferably is enclosed in a housing 18, to protect the device. The housing preferably also includes ducting 19a connected to a blower 19b and HEPA or other filter 19c. The filter provides clean air to the blower which can keep the housing under a slight positive pressure during use, thus preventing dust, mold, and the like from entering the atmosphere of the device. This embodiment of an autoconnect device works in the following manner. A user furnishes one or more containers of dialysis fluid and tubing for the containers, the tubing including a special cap for connecting via the autoconnect device. The tubing connects to the containers and the tubing is then connected to the dialysis machine via a disposable cassette. The special cap is placed into the near side of the rotating finger and the tubing is laid into the channel atop the autoconnect device. The autoconnect device then begins its automatic sequence for connecting one or more containers of dialysis fluid to the dialysis machine.

The occluder translates to the left, thus grasping the tubing and holding it immobile within the shuttle. The shuttle translates forward, and each finger with a cap causes that finger to rotate forward, in the direction of the shuttle movement. The movement of the finger causes the finger to grasp the cap from a port on the disposable cassette. The shuttle is now translated backward, away from the disposable. The finger, with the tubing cap atop, is captured by the port cap. When the shuttle translates backward, the tubing cap is removed because it is restrained within the finger. After the shuttle translates backward, the fingers rotate in a backward direction. Since the cap or caps from the disposable ports are captured by one or more fingers, this rotation removes the cap or caps. Further rotation below horizontal causes the caps to fall from the finger or fingers into a bin or open area below the fingers.

Movement of the shuttle, the occluder, and the fingers is controlled by a controller or microcontroller of the autoconnect device. As part of the controls, the shuttle is equipped with an optical sensor 24a, mounted on the bottom portion of the shuttle. The optical sensor 24a is guided by a stationary sensor track 21b, mounted in parallel with the lead screws. Sensor track 21b includes a series of notches as shown. The notches allow the optical sensor to keep the controller informed of the position of the shuttle. As will be obvious to those with skill in the art, other sensors or techniques may be used, such as an encoder on shuttle motor 22, a proximity sensor mounted on the shuttle and targets placed at appropriate locations along the shuttle path, and so forth. For example, a hall effect sensor mounted on the shuttle may be used to detect its position by placement of magnets or other targets along the shuttle path. Alternatively, a position sensor for detecting a position of the shuttle may be placed on the frame with notches, magnets, or the like placed on the shuttle.

Fluid Containers and Disposable Cassettes

The autoconnect device is not limited to the embodiments above. For instance, other dialysis disposable cassettes may include the model depicted in FIG. 3A. Disposable cassette 30 includes a front portion 31, heating tube 32 and five ports 33 for connecting to dialysis fluid connectors. Each port includes a cap 34 with a protruding, stepped central portion 34a. This protruding portion makes it easier for the autoconnect rotating fingers (discussed below) to grasp the cap. Port 35a is used for input/output lines to and from the patient, and port 35b is used for a drain. This particular model of a disposable cassette may require an autoconnect device in which the tubing on the shuttle is oriented in a vertical direction, rather than in a horizontal direction. The shuttle will still translate back and forth toward and away from the cassette, and the occluders will translate in a direction perpendicular to the movement of the shuttle. The fingers will be oriented for rotation in a horizontal plane, rather than vertical. When the caps are removed, they will fall away from and to the right of the autoconnect device. The ports have spikes, visible in FIG. 3B below.

The port caps 34 have symmetry, preferably radial symmetry. The caps are also preferably radiation-sterilizable and steam-permeable, and are made from low density polyethylene (LDPE). LDPE is able to form a tight seal against the cassette port, protecting the sterility of the port. Other relatively soft materials may be used, but the stepped tips or nipples should be able insert themselves within the jaws of the rotating fingers. Other embodiments may use non-stepped nipples or central portions. The wider next portion of the nipple causes a slight interference with the jaws, and allows the caps to be pulled off the ports when the fingers rotate downward. Besides LDPE, other materials may be used, such as PVC, (poly-vinyl chloride), polyisoprene, silicone and other suitable sterilizable materials.

Figure 3B:
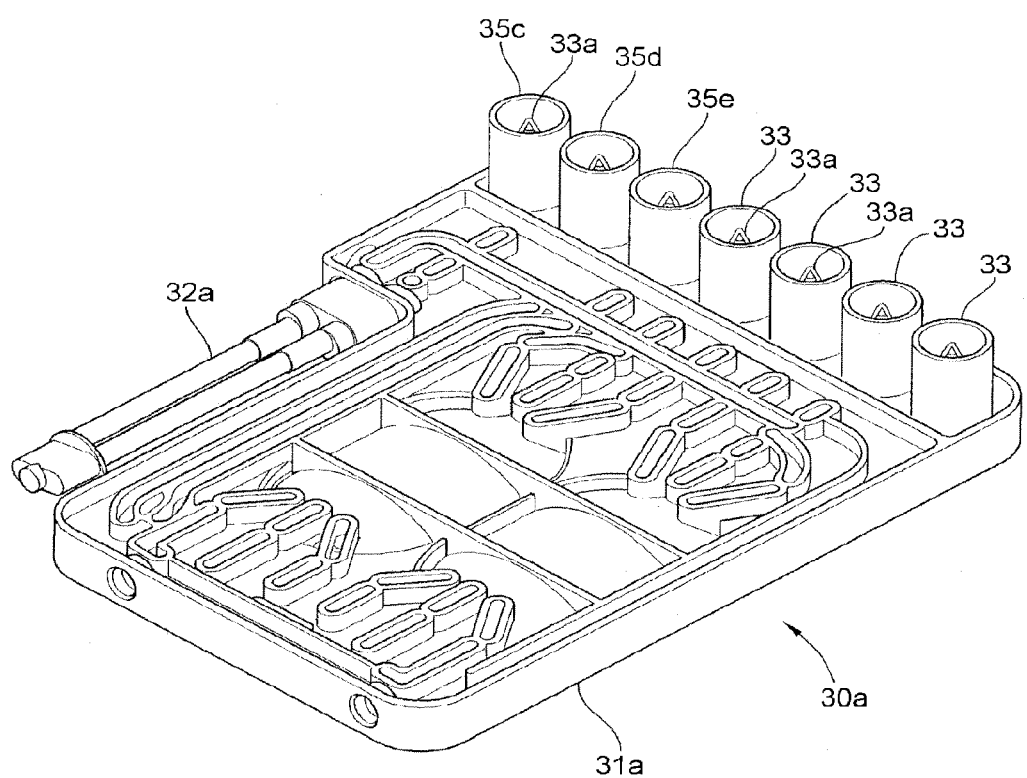

FIG. 3B is an alternate embodiment of a cassette suitable for use with an autoconnect device. Cassette 30a is similar to cassette 30, in that it includes a front portion 31a (shown), a back portion (not shown), a heating tube 32a, and four ports 33 with spikes 33a for containers. In addition, port 35c is provided for connection to the patient, and port 35d for the drain, and port 35e is used return from the patient. The other ports also have spikes 33a for making tubing connections. Rather than using the same port and line for to and from the patient, separate lines are used to help preserve the purity of the dialysate or other fluid. For example, pediatric patients may use much smaller volumes of dialysate, and much smaller volumes for recirculation. With very small babies, volume could be as low as 50 ml, while the spent dialysate in the tubing to/from the patient and the cassette could be as much as 15 ml. Separate lines to and from the patient avoid reuse of spent dialysate to the maximum extent possible.

Figure 4A:
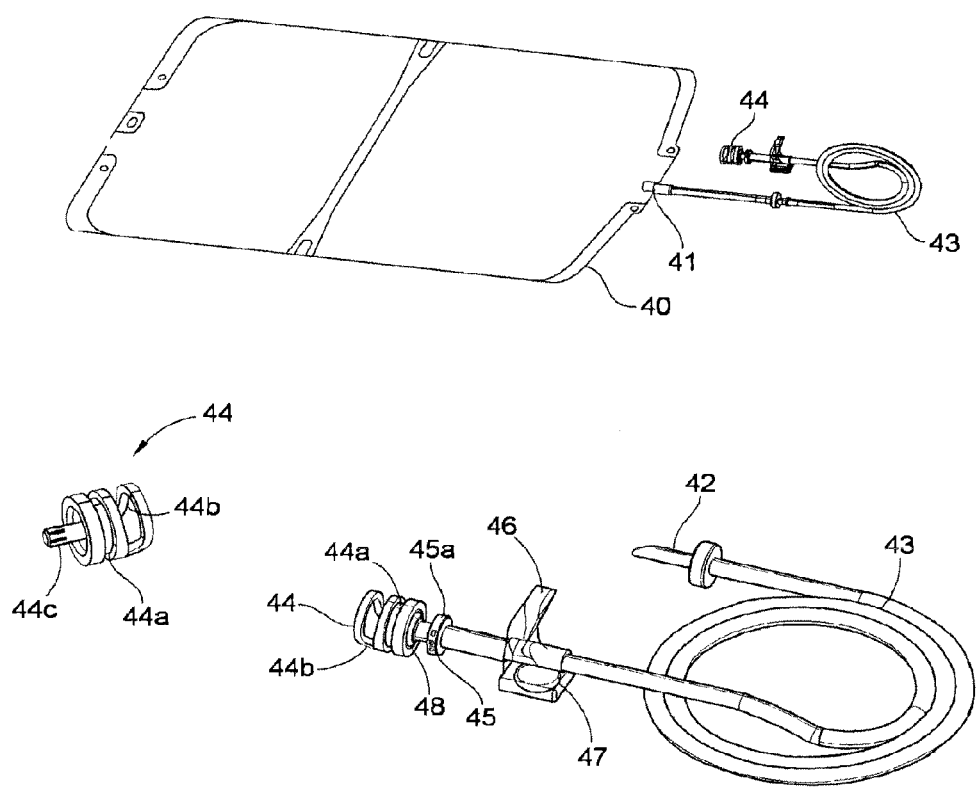
FIG. 4A is an exploded view of a container of dialysis fluid, tubing for use with the container, and a cap for maintaining a sterile end of the tubing.

A closer view of a typical dialysis fluid container is depicted in the exploded view of FIG. 4A. Dialysis bag 40 includes an outlet connection 41 and is used with tubing 43 and a tubing connector 42 for connecting to dialysis bag 40. Tubing 43 includes a housing 46 for a radio-frequency identification (RFID) tag 47. RFID tag 47 is used to identify this particular container and lot of dialysis fluid when the tubing is placed into the autoconnect device and the tag is read. The tubing also includes a flanged handle 45 and a membrane port 45a (internal to the tubing) or internal seal. Tubing 43 is terminated with a cap 44, the cap including a groove 44a, a fold-down handle 44b, and a core pin 44c. Groove 44a is preferably about 2.5 mm wide and about 2.0 mm deep. The handle is useful for removing the cap manually if an autoconnect device is not available. The core pin 44c is used for interfacing and with the internal portions of tubing 43, to preserve the dimensional stability of the tubing up to internal membrane 45a.

The tubing 43 and membrane port 45a may be made from PVC, and the tube cap 44 is preferably a relatively soft material, both the tubing and the tube cap steam are preferably steam sterilizable and steam permeable materials. Very soft silicone, with a Shore A durometer reading of about 35 is preferred, although other materials, with a durometer from 50-100 may also be used. Polyisoprene may be used, as may many styrenic block copolymers, such as those produced by Kraton Polymers, LLC, Houston, Tex., USA. Any of the softer, steam permeable grades will work well in the application. In one embodiment, tube cap 44 may also serve as the RFID housing.

RFID housing 46 is easier to handle and install in the translating shuttle if the housing is a little stiffer. For example, the housings may be made of HDPE, polycarbonate, harder PVC, or other material with a higher Young's modulus. If housing 46 is more rigid, it is easier to insert into the channels of the autoconnect shuttle. The RFID housing need not take the shape disclosed herein, which is configured for ease of placement onto the shuttle. The housing may be any convenient and useful shape that will reliably adhere to the tubing or even to the bag of fluid. In some embodiments, the RFID chip is placed into the housing in a secure manner, such as with a snap-fit. In other embodiments, the RFID chip is insert or over-molded into the housing. In the embodiments disclosed below, the RFID housing is configured for placement over the tubing, for ease of installation onto the shuttle. In other embodiments, the RFID housing may be placed or adhered onto the bag or container of fluid, and is read by a single RFID reader on board the frame or the shuttle. The autoconnect system then directs the user to connect the tubing to a particular channel on the shuttle. Thus, the controller knows the location of each connector and how to utilize each container.

Figure 4B:
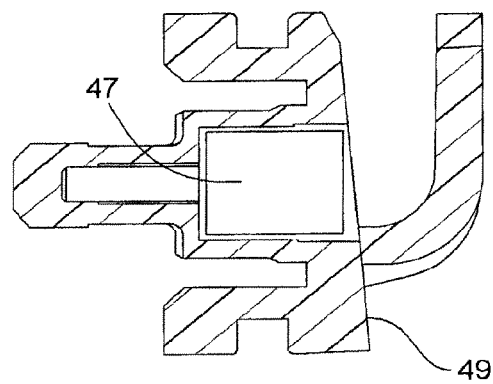
FIGS. 4B and 4C are alternate embodiments of a cap with an RFID chip or other direct part marking feature.
Figure 4C:
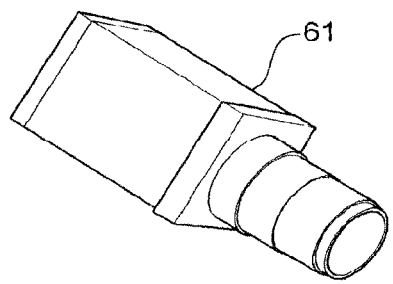
Figure 4C:
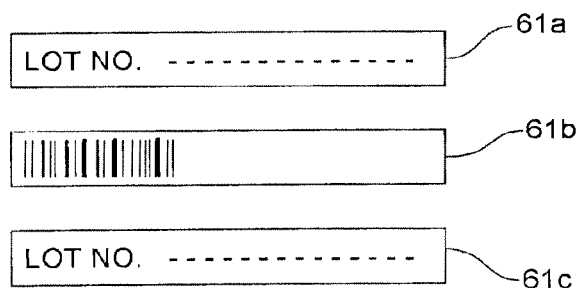

In some embodiments, as shown in FIG. 4B, the RFID chip may be assembled or otherwise installed into the cap itself, without a separate housing for the RFID chip. Using this technique, each rotating finger 27, as shown in FIG. 2, will include an RFID reader, to read the chip and report back to the autoconnect controller. Thus, tubing cap 49 will include RFID chip 47 and will be read by an IR reader in the finger 27 in which the cap is placed. In other embodiments, the cap of the tubing, or even the tubing itself, may include a mark as shown in FIG. 4C. In versions using direct parts marking, appropriate information about the solution to be administered, such as the solution, the lot number, and so forth, may be marked onto the cap or the tubing directly. Marks may be made by imprinting, for example, by stamping or ink-jet or other printing method, as shown by imprinted mark 61a. Marks may also be made by placing a bar code indicia, 61b, or by etching a mark 61c. Etching may be accomplished by laser marking, for example. The marked cap or tubing may be detected by a camera 61 mounted on the autoconnect frame and operably connected to the autoconnect controller or the dialysis machine controller.

Placement and Identification of Tubing and Operation of the Occluders

Figure 5A:
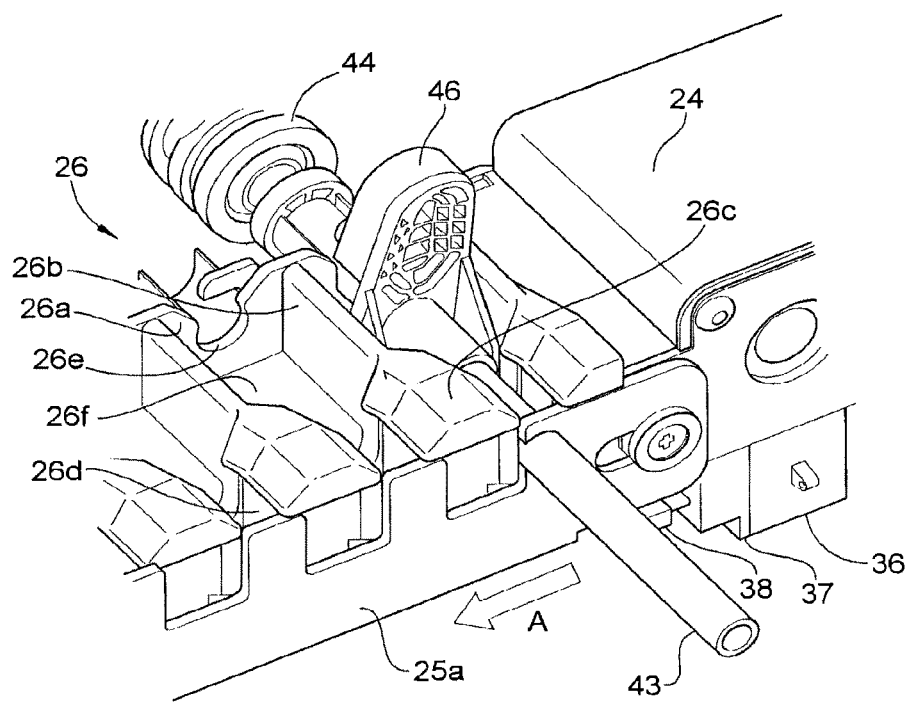
FIGS. 5A, 5B and 6 depict the occluder and the occluding mechanism.
Figure 5B:
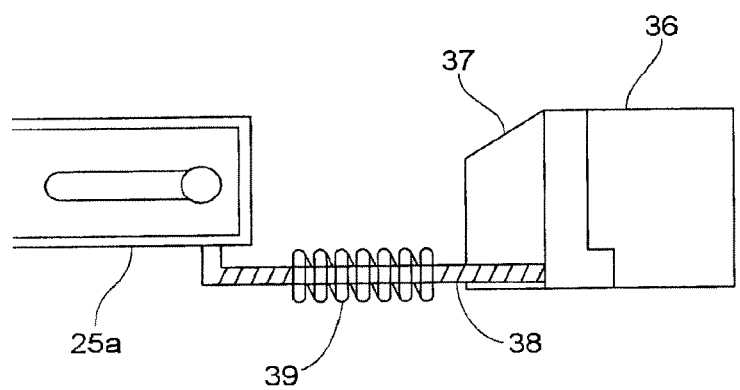
Figure 6:
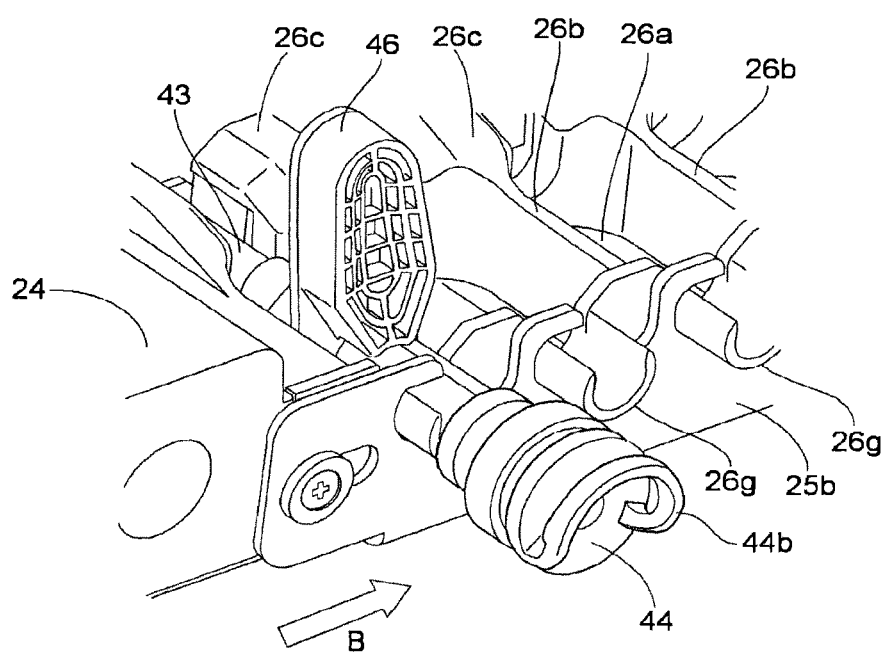

The placement of tubing from the dialysis containers, or tubing from other containers, is depicted in FIGS. 5A, 5B and 6. FIG. 5A depicts a view of shuttle 24 from the tubing side, while FIG. 6 depicts the view from the opposite or disposable side. FIG. 5B shows a close-up of the occluder drive mechanism. Autoconnect device central area 26 includes one or more channels 26a for tubing. Each channel 26a includes side walls 26b with shroud 26c, back end wall 26d, front end wall 26e, and an RFID reader 26f. End walls 26d, 26e include rounded orifices to accommodate the tubing. In one embodiment, the channels 26a and the RFID housing 46 are designed so that the RFID housing is retained in a releasable snap fit once it is inserted into the channel. The RFID reader is intended to read the RFID tag 47 placed in each RFID housing 46 as discussed above.

Occluder 25a has been translated to the left in the direction of arrow A, capturing tubing 43 between occluder 25a and shroud 26c. Occluder 25a is translated using a 6 VDC gear motor 36 mounted on the shuttle, with a suitable speed reduction gearbox 37 and a lead screw 38 mounted to the occluder. Both occluders move at the same time. In some embodiments, spring 39 may used to bias the occluder to a closed position. In other embodiments, the spring may be placed, for instance on the opposite end of the occluder, to bias the occluder open. In yet other embodiments, the control circuitry may include a large capacitor to assure sufficient energy to drive the occluder to a safe closed position as a fail-safe mechanism. At this point, the seals upstream of the tubing may not have been broken, and there may be no fluid in the tubing. The purpose of the occluder, or grasping mechanisms, is to occlude the tubing lumen and also to grasp the tubing to advance the tubing or, as will be seen, to retract the tubing and automatically remove the tubing cap. It will be understood that a solenoid or an air cylinder, or other mechanism, may be used to slide the occluder back and forth on its mounts or mounting pins rather than a lead screw.

Some embodiments may not use occluders. As discussed below, the tubing from the container fits tightly into a housing for an RFID chip. With only a small amount of friction, the tubing will adhere to the RFID housing and will follow along when the RFID housing is placed onto the shuttle. The tubing will also remain in place in the housing when the shuttle is advanced a short distance back and forth within the frame to remove the tubing cap and to pierce the tubing membrane. Some embodiments may thus not use occluders, but the tubing will still travel with the shuttle, moving when the shuttle moves under the influence of normal friction between the housing and the tubing. It any event, the occluder may be useful for other reasons, such as preventing loss of fluid during spiking, or allowing the controller to conduct connection integrity tests. Failsafe closure, described above, may help prevent cross-contamination in case of a power failure.

RFID chip housing 46 is sized to fit within channel 26a, possibly with a snap fit. As seen from FIG. 6, from the opposite side of shuttle 24, back occluder 25b has been translated to the right, in the direction of arrow B to capture tubing 43. While arrows A and B seem opposite, the directions are the same because FIG. 5A views the shuttle from the tubing side, while FIG. 6 views the shuttle from the disposable cassette side. Each channel 26a includes a front collar 26g extending toward the cassette. In addition to the collapsible handle 44b on the tubing end 44, RFID housing 46 may also serve as a handle for placing tubing in the channel. The RFID chip should be durable and rugged, and should be able to withstand sterilization, whether by gamma-ray irradiation, steam autoclaving, typically conducted at about 1 atm gage pressure at 121° C., or by chemical methods.

RFID tag 47 (not shown in FIG. 6) includes an antenna that may, or may not, be coupled to an integrated circuit chip or chip that can store or contain additional product information, tracking information, shipping information or any other desired product information. In operation, the processor, powered by the power source, provides a signal that is transmitted by the transceiver. The transmission energy of the signal communicated by the transceiver serves to inductively and communicatively couple the RFID tag 47 to the reader 26f. Reader 26f is essentially a small circuit board with circuitry for communicating with RFID tag 47. The circuitry usually includes its antenna, a controller or control circuit, and input/output circuitry for communicating with the autoconnect controller. When the RFID reader sends a signal, an electrical current is, in turn, inductively generated within the RFID tag antenna. The electrical current can serve as a "zero bit" to simply indicate the presence or absence of the RFID tag 47. Alternatively, the electrical current can power the chip, thereby allowing the additional information stored thereon to be communicated between the RFID tag 47 and the reader 26f. In one embodiment, RFID tag 47 records an indication each time the tag is read. In one embodiment, RFID tag 47 records and stores additional information from the system controller, including at least one of a patient identifier, an amount of dialysate or liquid administered, a date and time, and other helpful medical information.

The RFID tag 47 as illustrated is a passive tag, which includes no internal power source and instead is inductively powered and interrogated by the reader. In application with the present disclosure, RFID tag 47 can alternatively be a semi-passive device that includes a battery that is printed onto the substrate. The addition of the printed battery power source allows the antenna to be optimized for communication, as opposed to current generation. In another embodiment, the RFID tag can be an active tag that includes a long-life battery, one or more integrated circuits, display elements, storage elements, etc.

In some embodiments, the RFID tag 47 includes a transponder that operates at a relatively low frequency, about 125 kHz to about 134.2 kHz, or from about 140 kHz to about 148.5 kHz, and having a read range of as low as about one inch. A high frequency transponder typically operates at about 13.56 MHz with a read range of up to a meter. Further, transponders may even operate at an ultra-high frequency, such as 433 MHz, or typically between about 868 MHz to about 928 MHz, with a read range of about 3 m or beyond, such as those used for electronic toll collection and the like. In the present application, small, low frequency RFID tags with very short range are preferred, so that each tag is identified within its channel or range on the shuttle or other part of an autoconnect system. These ranges will preferably be less than one inch, in the range of about 20-25 mm. The reading range depends on the design of the reader or interrogator and can be kept short.

For purposes of the present disclosure, and regardless of physical configuration, an RFID tag includes any device configured to communicate information via radio waves transmitted at frequencies of about 100 kHz or higher. In fact, the operating frequencies of individual tags can be considered a secondary consideration given that the overall structures of typical tags are very similar. The RFID tags allow positive identification of each bag or container whose tag is placed into the shuttle. With this technique, the autoconnect controller, or the controller for the dialysis or other system, will know whether the placement made is correct and incorrect and notify or alert the operator or other personnel when an incorrect placement is made.

The above discussion focused on placing the containers of dialysate fluid, and their tubing and connectors, and automatically identifying the containers using RFID tags. It is clear from the above discussion, that other positive techniques may be used for identification, such as bar code labels or indicia on the tubing ends, and a bar code reader on the autoconnect device. Still other techniques may be used, such as i-buttons from Maxim Integrated Products, Sunnyvale, Calif. An i-button, similar to an RFID, is an integrated circuit with a unique identification, contained in a small, flat, metallic package. An i-button identification circuit usually requires touching to an i-button reader, but the principle of automatic and unique identification is similar to that used with a bar code or an RFID tag. It will also be obvious to those with skill in the art that the autoconnect device may be operated with no automatic identification feature, such as RFID tags or barcodes. Identification of the fluid dispensed may be made manually or by entering a information, such as a code, manually into a computer for tracking patient care.

Making Connections and Preserving Sterility

Figure 7:
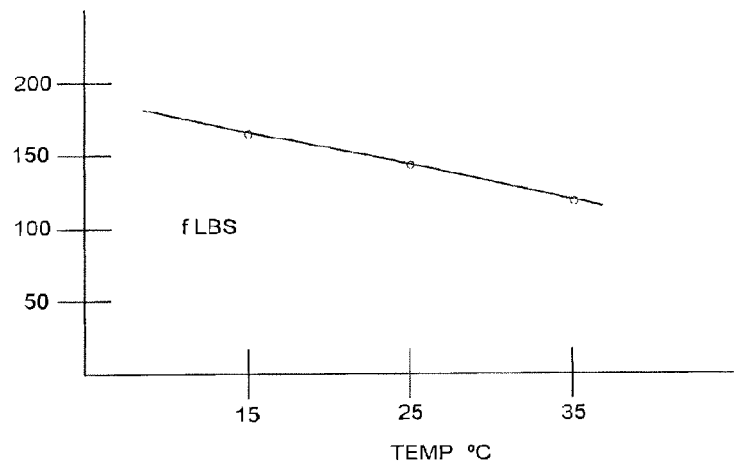
FIG. 7 graphs experimental results for the force needed for connecting containers of fluid.

Once the tubing is in place, the tubing is connected so the fluid in the containers can be dispensed or otherwise distributed or used. FIG. 7 illustrates graphically the problem in connecting bags of dialysis solution to the disposable cassette. The upper line with three points represents testing at different temperatures, while the lower line represents testing with an improved spike design. The force required for connecting four bags at room temperature, 25 C, was about 140 lbs, or about 35 lbs force for each connection, which connections are of course made by hand, one at a time. At cooler temperatures, 15 C, the force for all four was about 160 lbs, or about 40 lbs force each, while at 35 C, the force dropped to about 120 lbs, or about 30 lbs force each. Even with the improvement of a stepped spike, as discussed for FIG. 8A below, the force required is still about 80 lbs, or about 20 lbs force for each connection.

Figure 8A:
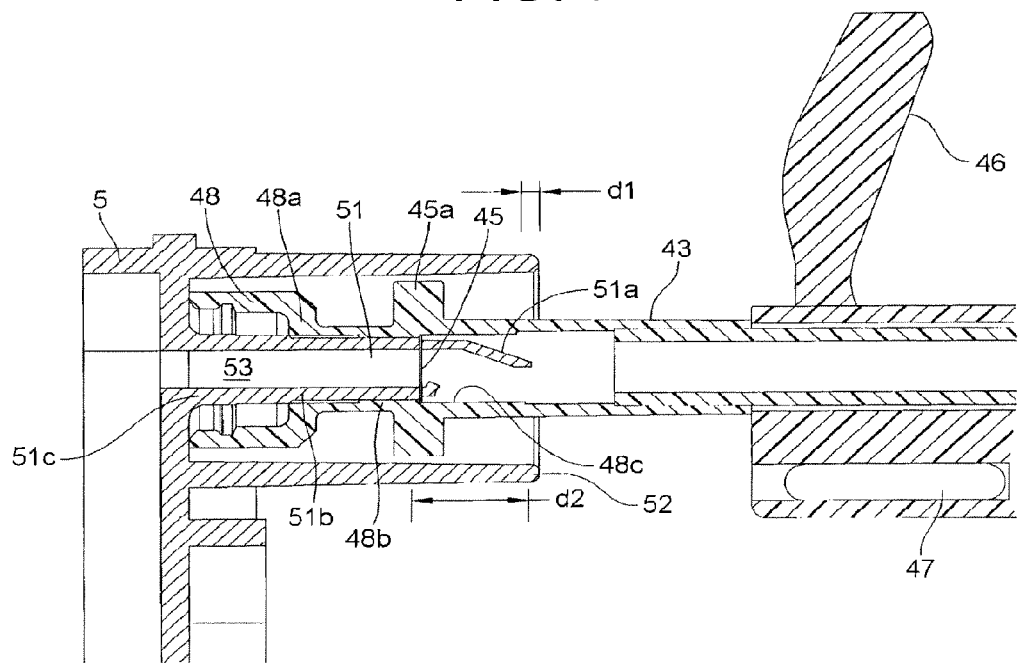
FIGS. 8A, 8B and 8C are a cross-sectional views of engagement between a containers of fluid and spikes, such as those from a pumping cassette.

FIG. 8A depicts the improvement in the spikes discussed above and also illustrates a technique used to insure that the connection between the disposable cassette and the tubing remains sterile. In this cross sectional view, tubing 43 with RFID housing 46 has been placed in position and membrane seal 45 has been penetrated and broken by hollow spike 51 of the disposable cassette port 52. The outer diameter of the distal portion 51a of the spike is less than the outer diameter of the spike main portion 51b, which may be slightly less than the diameter of spike proximal portion 51c. In addition, tubing end connection 48 may include three stepped portions, distal portion 48a with a larger inner diameter, mid-portion 48b with a smaller inner diameter, and proximal portion 48c with a larger inner diameter, which provides clearance for material from the penetrated seal to fold or hinge out without occluding the lumen and without requiring additional force to complete the penetration.

Spike 51 is contained within port 52. Spike 51 includes an inner lumen 53 so that when spike 52 penetrates membrane 45, a fluid connection is established between the dialysate solution bag tubing 43, and disposable cassette 5. The parts are designed so that the connection between sterile parts is made before the membrane seal of the tubing is broken, thus preserving sterility of the connection. The spikes are preferable a relatively hard plastic, such as acrylic, polycarbonate, or acrylonitrile-butadiene-styrene (ABS). Cyclic-olefin containing polymers (COCs), especially those blended with ULDPE, may also be used for the cassettes and spikes. See, e.g., U.S. Pat. No. 7,011,872, assigned to the assignee of the present patent, and which is hereby incorporated by reference.

The distal portion 51a of spike 51 does not extend beyond the outer rim of port 52, i.e., the spike is shrouded within the port. In this embodiment, port 52 extends a distance $d_1$ beyond spike 51 and spike distal portion 51a. This helps to prevent inadvertent touching and contamination of the spike after the port cap is removed. When tubing end connection 48 is seated within port 52, the distal portion 51a of the spike extends within tubing 43 for a distance $d_2$.

Spike distal portion 51a, as shown, has a smaller outer diameter than spike mid-portion 51b. As noted above, tubing connection 48 inner portion 48a has a larger inner diameter. When tubing 43 is connected to port 52, spike distal portion 51a with a small outer diameter encounters connector portion 48a with a larger inner diameter. In this embodiment, and as seen in FIG. 8, the outer diameter of the spike portion 51a is less than the inner diameter of connector inner portion 48a, allowing the spike to pass through without interference. Upon further insertion, when connector inner portion 48a encounters spike mid-portion 51b, a seal is made between them just before the spike tip penetrates seal membrane 45. After penetration, spike mid-portion 51b seals against tubing mid-portion 48b. In addition, an outer seal is made between tubing proximal portion 48a and spike proximal portion 51c at the entrance to the tubing, i.e., the entrance to tubing portion 48a.

This arrangement of a stepped spike and stepped connector tubing minimizes insertion forces while simultaneously minimizing opportunities for contamination of the connection parts. It will be recognized that other spikes may be used, such as tapered, non-stepped spikes, as well as tapered, non-stepped spikes with a leading edge on one portion of the spike arc. It will also be recognized that some spikes may have a sharp edge, while others will be blunt. Using a blunt edge helps to prevent injuries. In the present embodiment, designed for no contact with a person using or operating the autoconnect system, sharp edges are preferred, for minimizing the force necessary to make the tubing connections.

Figure 8B:
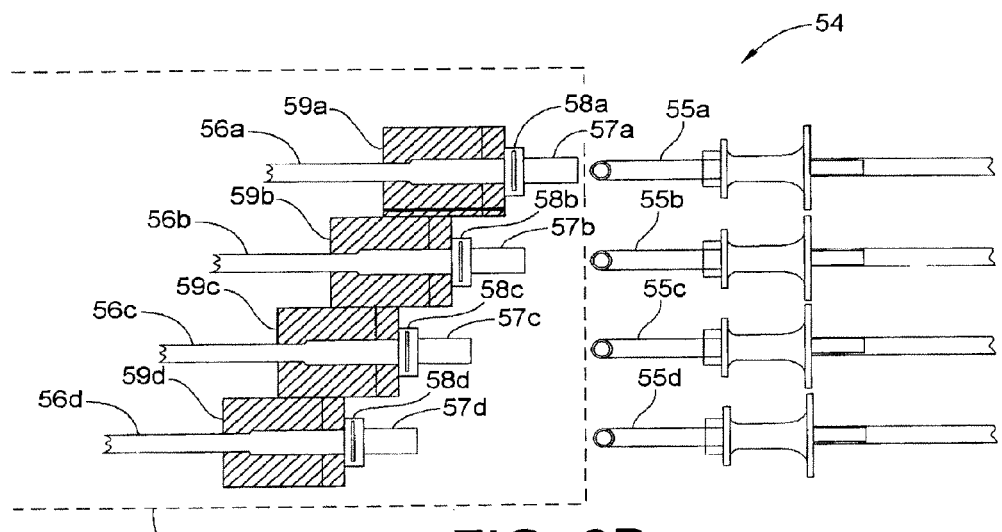
Figure 8C:
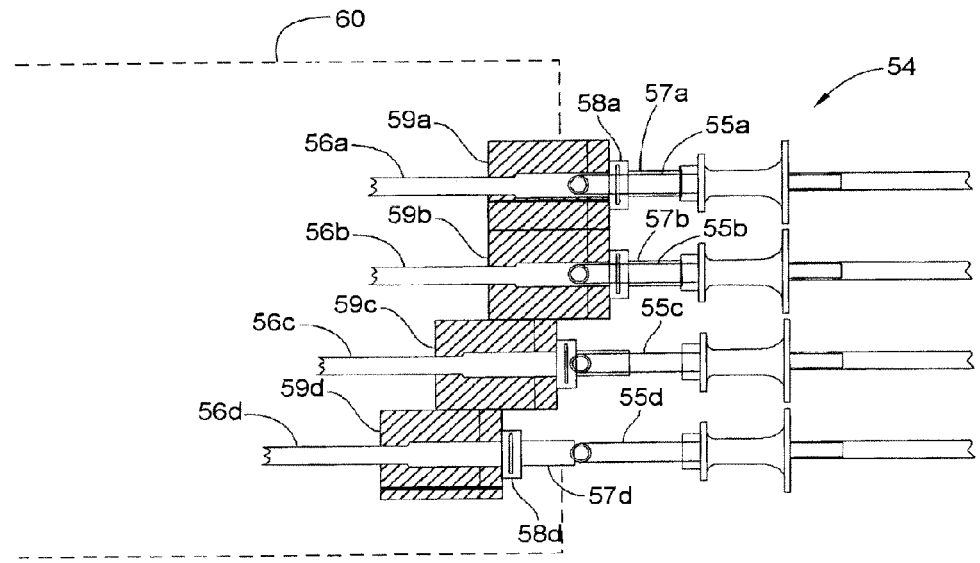

FIGS. 8B and 8C depict an autoconnect mechanism in which the tubing tips approach the cassette 54 and spikes 55a-55d for sequential spiking. In this embodiment, shown with the tips of four containers of medical fluid, the autoconnect mechanism has four independently-moving tips, 57a-57d, from four containers with outlet tubing 56a-56d. Each tip has a membrane or seal 58a-58d for spiking by the spikes 55a-55d. The tubing and tips are mounted in independently-moving mounts 59a-59d on a stationary platform 60. As discussed below with respect to FIGS. 19-21, separate movement for each mount may be provided by suitable devices, such as solenoids, air cylinders, electric motors, or even hydraulic cylinders. The mounts may be mounted on a shuttle or to tracks on the autoconnect frame directly. In this embodiment, the shuttle does not translate, but instead each device provides the separate back-and-forth movement described for the shuttle.

FIG. 8B depicts the four tips 57a-57d and mounts 59a-59d approaching spikes 55a-55d in a sequential manner. In practice, one tip may be advanced at a time. Preferably only one spiking connection is made at a time. As seen in FIG. 8C, the top two tips, 57a, 57b and membranes 58a, 58b, have been spiked, one at a time, by spikes 55a, 55b. The third tip, 56c, is approaching the third spike 55c, and the fourth spike will be next. By using sequential spiking, the total force required for penetration of the membrane by each spike is spread over four time sequences, rather than all at once. Thus, the motor, cylinder, or solenoid that advances each mount may be smaller, since it needs only enough force to penetrate one seal, about 20-25 lbs force. Alignment of the mounts with the spikes may also be easier, since each mount, in its own channel or pathway, need only align with a single spike. Even though there may be a plurality of mounts and pathways to align, there are just as many to align in embodiments with a translating shuttle.

The above discussion focused on automatically making the connection between containers of dialysate fluid and the inlet ports of a disposable cassette. By analogy, the same technique with suitable geometries may be used for automatically making sterile connections between other containers of fluid and other dispensing or pumping systems. As previously noted, disposable cassettes may have their connection ports on the top of the cassette, or on the side. Of course, placement of the ports on the periphery of the pumping mechanism is preferable, whether top, bottom, side, or on an edge of the top, bottom, or side. The same principles apply to other fluid container connections, such as bags of blood or blood substitute being connected to an inlet port for a blood transfusion machine, such as a cardiopulmonary pump, bypass pump, or auto-transfusion machine. Still other applications are also possible.

Operation of the Fingers and Removal of the Caps

An important part of making the connections is the automatic removal of caps from both the tubing and the ports of the cassette or other pumping and dispensing mechanism. Automatic removal of the caps is an important part of the process because the caps, and the underlying ports and connections, may easily be touched and thus contaminated if the caps are removed by hand. Thus, as discussed above, special fingers are used to remove caps from both the product container tubing and from the ports of the pumping or dispensing machines, typically a disposable dialysis cassette.

Figure 9:
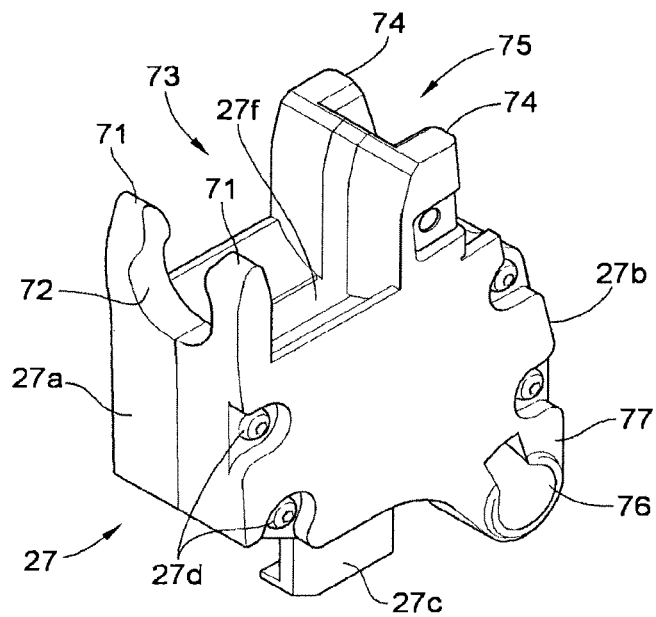
FIGS. 9 and 10 are rear and front perspective views of details of a first embodiment of rotating fingers for use in an autoconnect machine.
Figure 10:
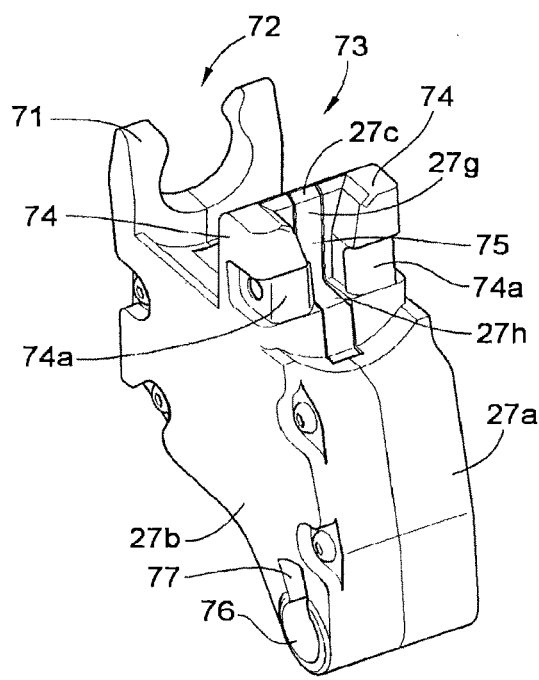
Figure 11:
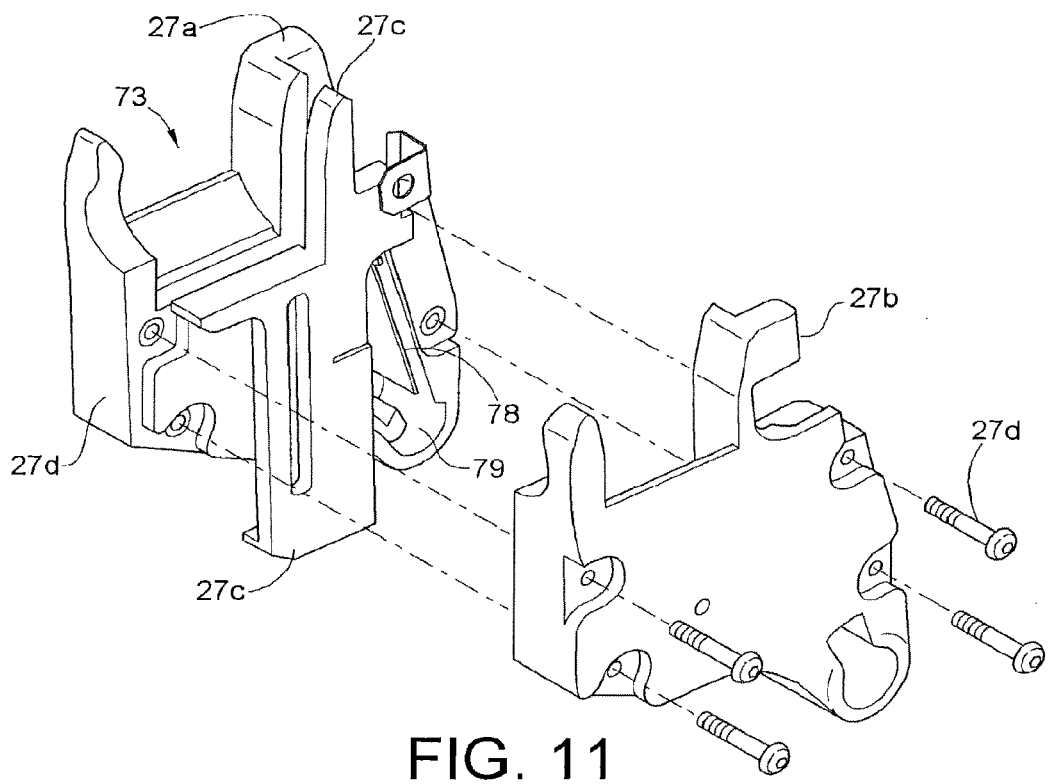
FIG. 11 is an exploded view of the embodiment of FIGS. 9 and 10.
Figure 12:
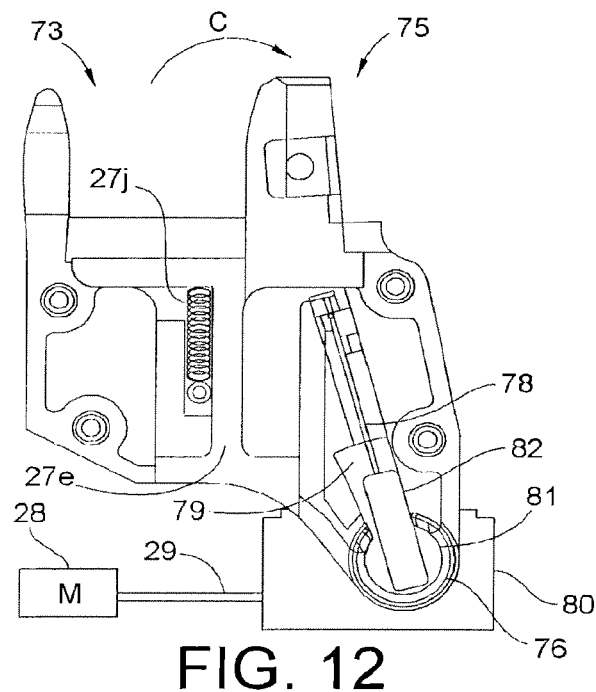
FIG. 12 is a side view of the embodiment of FIG. 9.

One embodiment of cap removal fingers is disclosed in FIGS. 9-14. FIG. 9 discloses a rear perspective view and FIG. 10 a front perspective view, of a finger 27 with left and right sides, 27a, 27b, a cap ejector plate 27c, finger 27 assembled with fasteners 27d. Ejector plate 27c is mounted within pocket 27 and travels via slot 27e within left and right sides 27a, 27b. In one embodiment, as shown in FIG. 12, a torsional spring 27j is mounted within finger 27 and under top surface 27f of the ejector to resist advancement of the ejector plate and to return it to the resting position shown in FIGS. 9-10. The top side of finger 27 includes a first pocket 73 with extended rails 71, the rails forming an orifice 72. Orifice 72 allows passage of tubing, as discussed above, but is smaller than the diameter of the cap for the tubing. The walls of rails 71 are curved, together forming about 290 degrees of a circle, i.e., the periphery of the cap, or the portion of the cap inside the outermost periphery, an inner periphery. This restraint allows the rails to retain the caps when the shuttle and tubing are retracted, as discussed above. The orifice is preferably at least about 180 degrees, and experiments have found that 290 degrees works well for removing caps. Other configurations with lesser coverage, such as several angularly spaced points, are also adequate for stripping the tubing cap from the tubing.

The top of finger 27 includes a second pocket 75, formed by extended rails 74 of left and right sides 27a, 27b. In this embodiment, the pocket 75 is formed by the rails 74 and by inserts 74a, spaced more closely than rails 74. The inserts are designed for grasping the center portion of a cap from a dispensing or pumping machine, such as a dialysis cassette.

As noted above, fingers 27 grasp the stepped, protruding nipple from the dispensing or port cap. The interference should be sufficient so that the cap is retained between the inserts. In one embodiment, inserts 74a are sharp near the center, so that when the finger 27 is rotated and the shuttle translated into the nipple of the port or dispensing cap, the inserts cut into the nipple portion, grasping the nipple portion. When the finger begins to rotate in reverse, the cap remains captive and is pulled away from the port. Also visible from both the top and bottom of finger 27 is an ejector plate 27c contained within the finger. Finger 27 includes a through shaftway 76 with a notched portion 77. A shaft rotates within the shaftway to rotate the fingers and to advance and retract the ejector plate. When the caps have been removed as discussed above, and are resting in pockets 73, 75, the finger is rotated and the ejector plate is advanced to eject the caps, all without touching and contaminating the tubing or the ports.

As seen in FIGS. 11-12, a shaft 81 actuated by motor 28 (see FIG. 1), input shaft 29 and gear train 80 extends through finger 27 and shaftway 76. Also contained within each finger 27 inner space 79 is a leaf spring 78, the leaf spring mounted against pin 82. Finger 27 can rotate relative to shaft 81, its travel limited by pin 82. The leaf spring 78 biases finger 27 to the back position, as shown in FIG. 12. There is sufficient clearance within space 79 so that pin 82 and leaf spring 78 can rotate back and forth, which limits travel, but also allows rotation of finger 27 in the general direction of the arrow C as shown, toward the cassette. When the shuttle is advanced, finger 27 rotates as shown and as allowed by the pin. In one embodiment, this is about 5 degrees. This is sufficient to allow the inserts 74a to grasp the port cap from a dialysis cassette port. Once rotation has taken place, the shuttle prevents reverse movement or rotation of finger 27. However, leaf spring 78 is engaged by rotation of the finger, and now urges finger 27 to rotate back, in the direction opposite arrow C. Thus, when the shuttle is reversed, and translates back, away from the cassette, finger 27 does indeed rotate away from the cassette, while gripping the port cap in second pocket 75 and removing it. The finger motor will cause the port cap to fall out as the finger is rotated down, out of the way. As discussed above, the cap from the tubing is held in first pocket 73.

Figure 13:
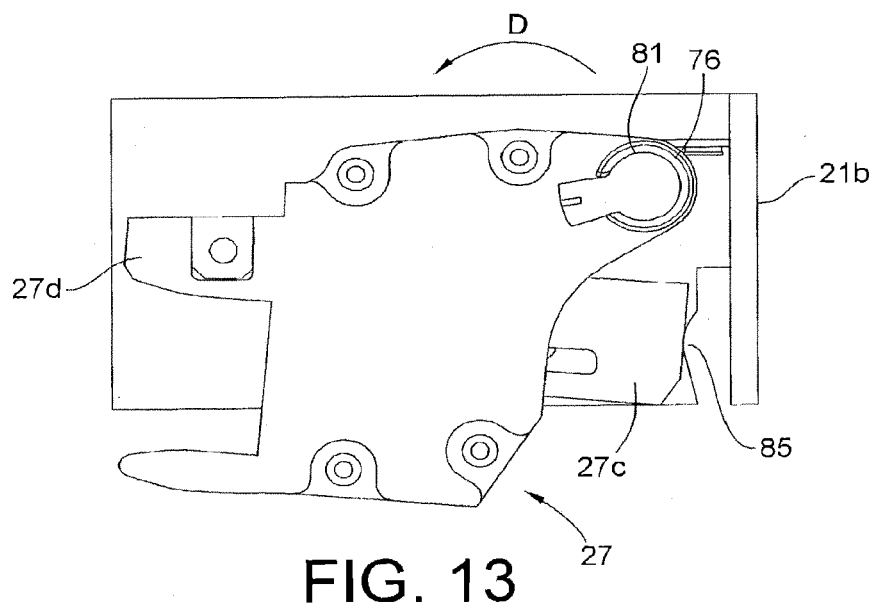
FIGS. 13-14 are additional views showing the functioning of the rotating fingers.
Figure 14:
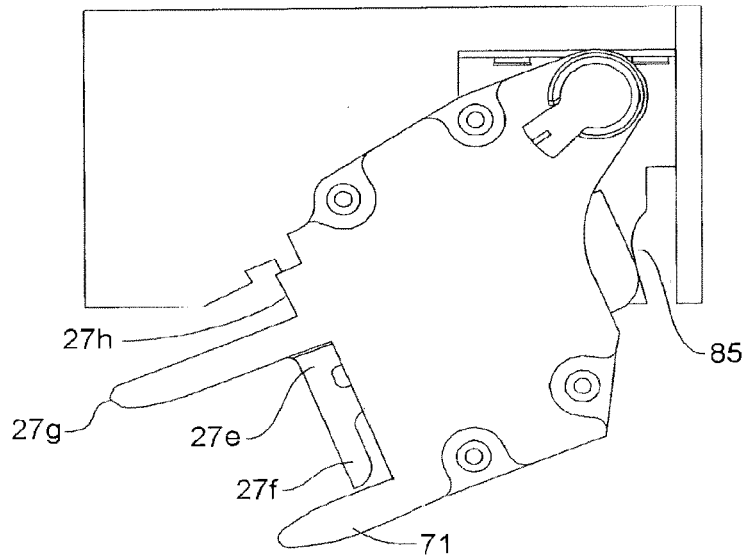

The caps have now been removed from the tubing and the port, and are disposed of before making the connections between the tubing and the port. FIGS. 13-14 depict rotation of finger 27 about shaft 81. After the shuttle has been translated back, away from the fingers, the fingers may be rotated downward to remove the caps. Output shaft 81 from gear train 80 rotates the fingers to actuate the ejector plate 27c and eject the caps from pockets 73, 75. Gear train 80 may include bevel gears on the shafts to turn motive power from motor 28 and input shaft 29 ninety degrees to rotate output shaft 81. In the alternative, a worm on the input shaft and a worm gear on the output shaft, or crossed helical gears will also work.

As finger 27 is rotated counterclockwise in the direction of arrow D beyond horizontal, ejector plate 27c will encounter protrusion or cam surface 85 on back wall 21a of the autoconnect frame. The interference will cause the bottom edge of ejector plate 27c to bear against cam surface 85, advancing ejector plate 27c through finger 27. As seen in FIG. 14, the top portions of the ejector plate, including a slide channel 27e top portion and top surface 27f, and a top ejector rear portion 27g, now protrude from the finger 27. Top surface 27f will eject a cap from pocket 73 and top portion 27h will eject a cap from pocket 75. The fingers will remain in the down position, out of the way, during therapy.

Overall Operation of an Autoconnect Device

Figure 15A:
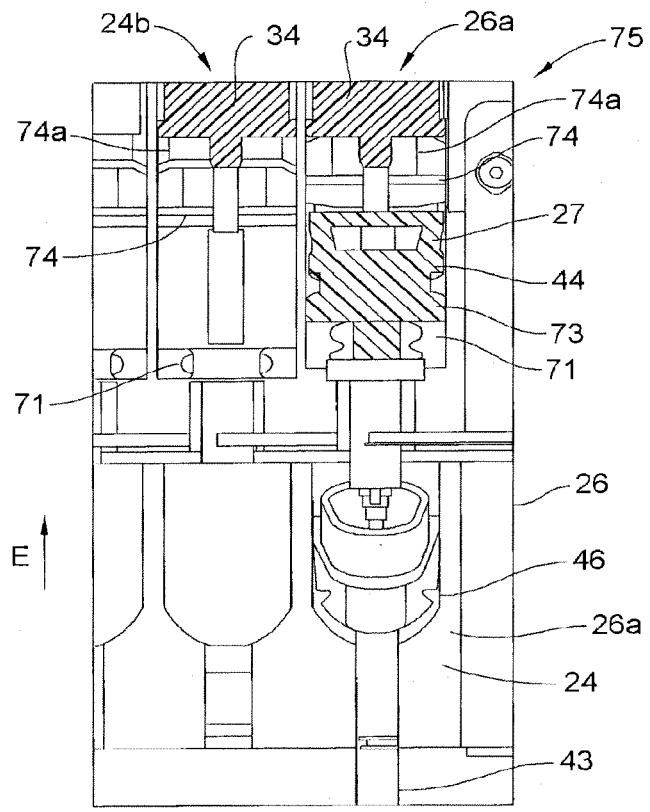
FIGS. 15A, 15B, 16A, 16B, 17A and 17B depict operation of an autoconnect machine.
Figure 15B:
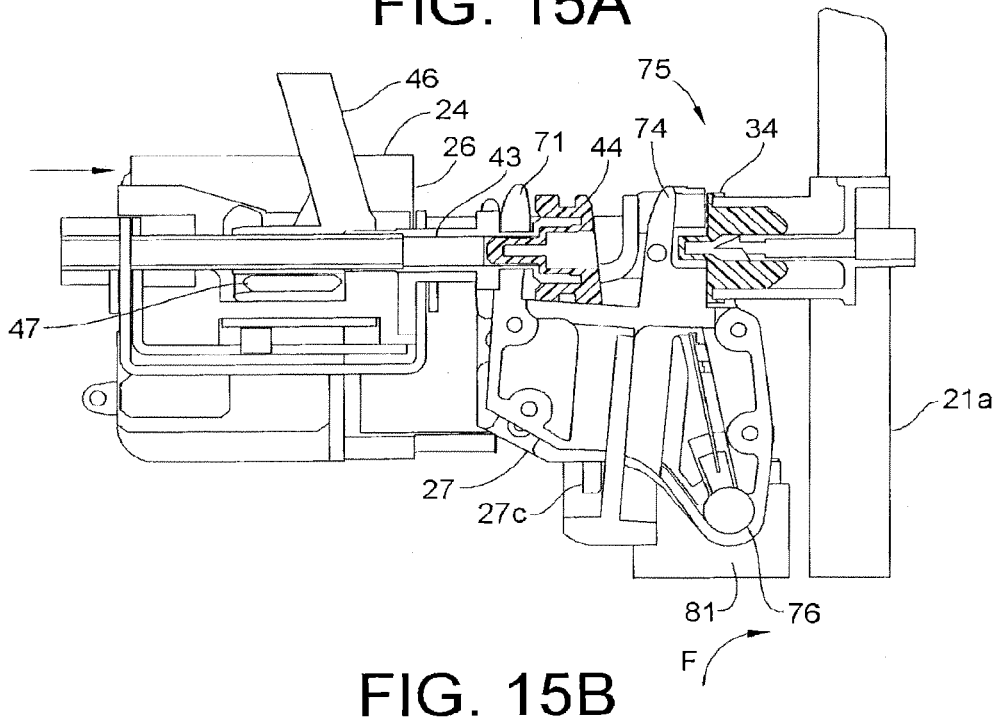

The above description may be better understood by disclosing sequential views of the operation. FIGS. 15-17 lead this discussion, and FIG. 18 provides a flow-chart version of the autoconnect process. In FIG. 15A and FIG. 15B, tubing 43 has been placed in a shuttle 24 channel 26a of central area 26, along with RFID housing 46 and RFID tag 47. For comparison in FIG. 15A, an unoccupied channel 24b, adjacent occupied channel 26a is shown, along with the fingers corresponding to the used and unused channels. Shuttle 24 has been advanced in the direction of arrow E, causing slight rotation of finger 27, but only the finger corresponding to channel 26a. This slight movement can be seen by the fact that rails 71, 74 of finger 27 in channel 26a have been advanced slightly.

As can be seen in FIG. 15B, this causes a slight clockwise rotation of finger 27 in the direction of arrow F and in the general direction of frame back wall 21a. As noted, finger 27 rotates about shaft 81 within shaftway 76. Returning to FIG. 15A, the slight rotation is sufficient for second pocket 75 to capture port cap 34, the port cap to the port and corresponding to shuttle channel 26a. This can be seen in top view FIG. 15A, as the port cap 34 is captured between extended rails 74. In contrast, in adjacent channel 24b, extended rails 71, 74 have not been advanced in the direction of arrow A, and extended rails 74 are not adjacent port cap 34 in the adjacent channel 24b.

Figure 16A:
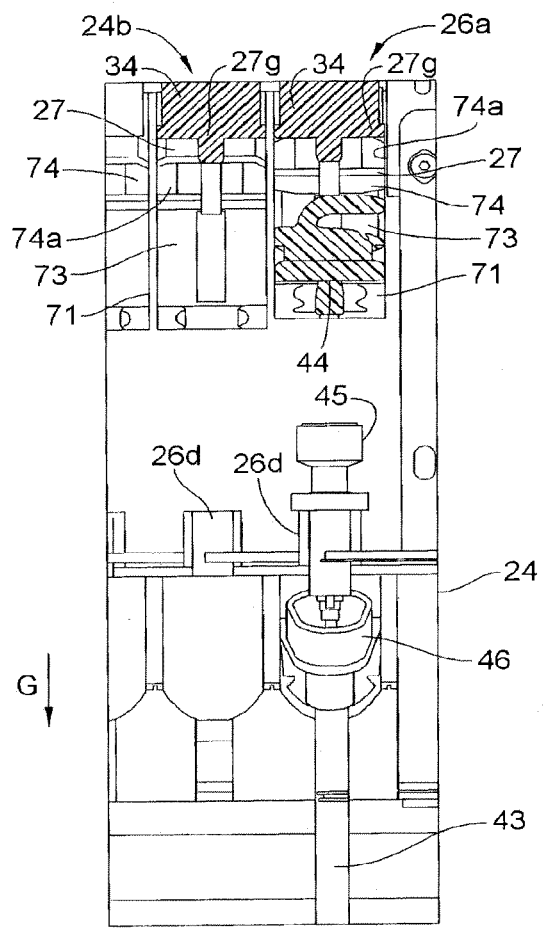
Figure 16B:
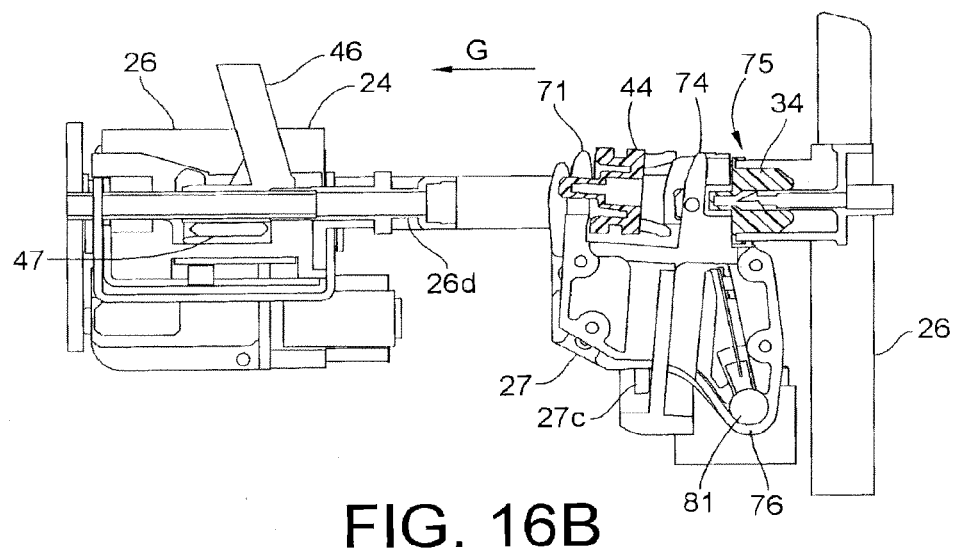

In FIGS. 16A and 16B, shuttle 24 has retracted in the direction of arrow G, away from frame back wall 21a. In channel 26a, but not in channel 24b, tubing cap 44 has been removed from tubing tip 45, the tubing cap retained in pocket 73 of finger 27. Finger 27 in channel 26a remains rotated rearward, as it was in the previous figures. Extended rails 71, 74 in channel 24b are thus offset from extended rails 71, 74 of finger 27 in channel 26a. Port cap 34 has been captured in pocket 75 of finger 27, but only in channel 26a, not in channel 24b.

Figure 17A:
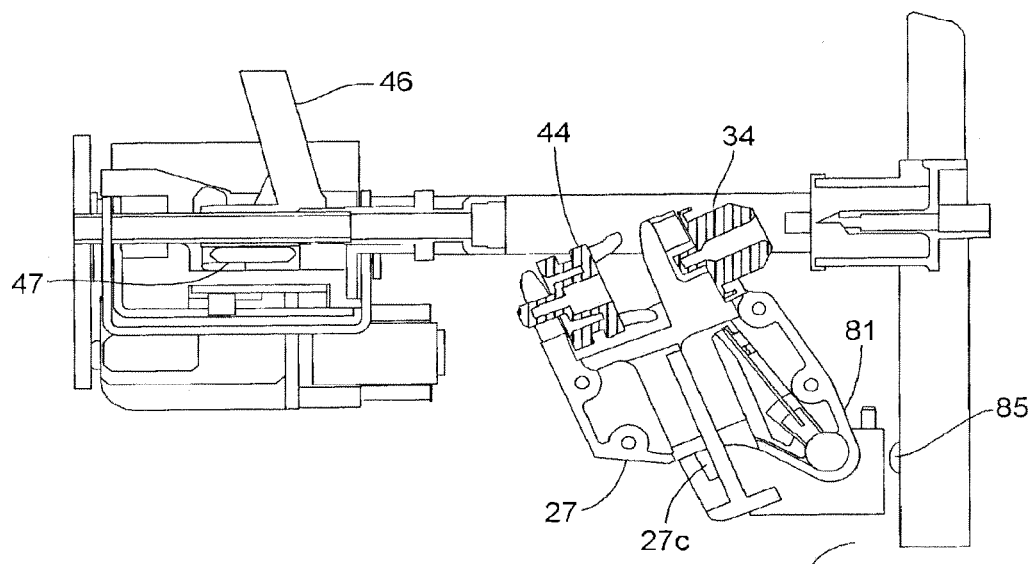
Figure 17B:
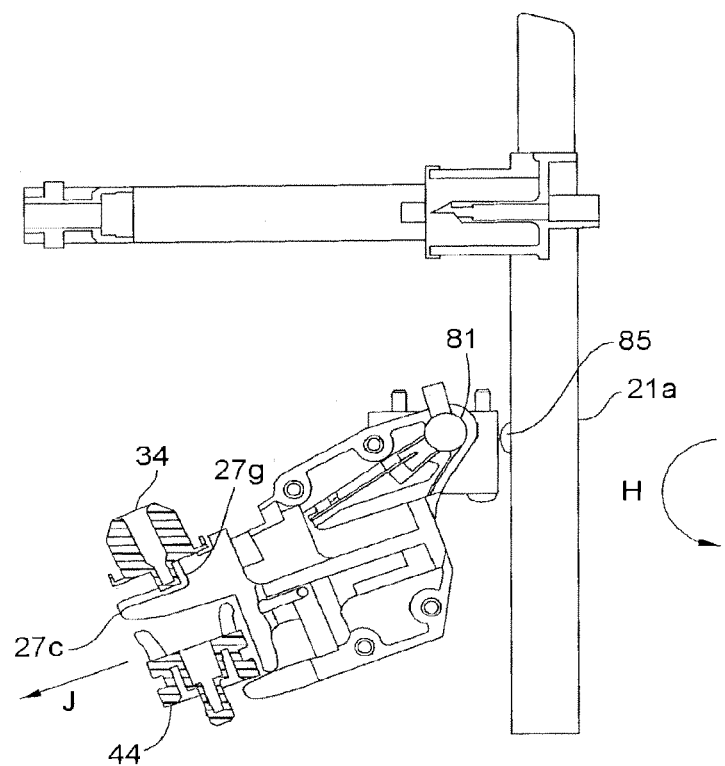
Figure 18:
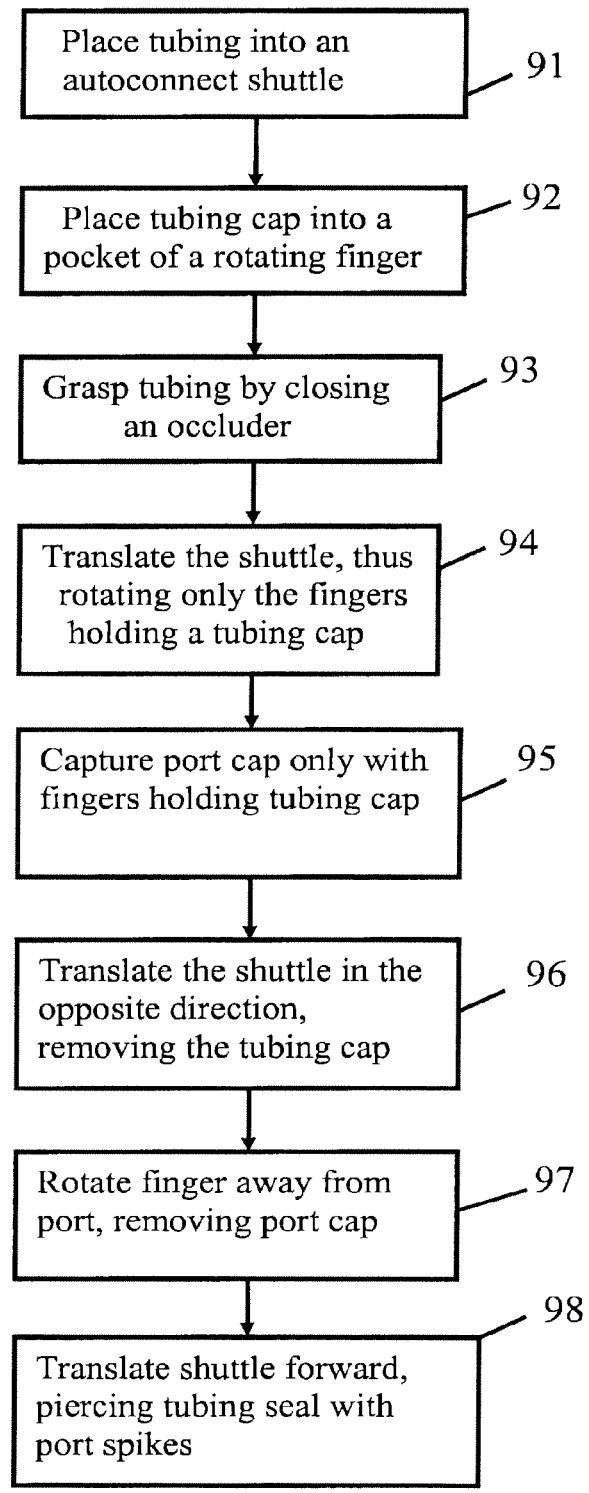
FIG. 18 is a flowchart for a method of operating an autoconnect machine.

FIGS. 17A and 17B illustrate the next two sequences in automatically removing the caps. Shaft 81 rotates counterclockwise in the direction of arrow H, causing finger 27 to also rotate. As the rotation continues, ejector plate 27c encounters a protrusion or cam surface 85 on back wall 21a, causing ejector plate 27c to advance within finger 27 in the direction of arrow J, causing the ejector plate to push caps 34a, 44 out of pockets 73, 75 and ejecting them from finger 27. After the caps are removed, and after therapy is concluded, the fingers can be rotated clockwise back to their normal position, opposite the direction of arrow H. In this embodiment, all the fingers are rotated, including fingers with no caps. In other embodiments, gearing or other power is arranged to engage only the fingers corresponding to channels with tubing.

The process as described above, for a method or process of automatically connecting tubing, is easily visualized with the aid of the flow chart of FIG. 18. The first step 91 is to place the tubing into an autoconnect shuttle. A cap of the tubing is then placed 92 into a pocket of a rotating finger. The tubing is grasped by closing 93 on the tubing with a holder or occluder. The shuttle is then translated 94 a short distance forward, moving forward tubing and the cap, along with the shuttle. This movement is sufficient to cause a slight rotation only of a finger which holds a tubing cap. When the finger is rotated, it captures 95 a port cap from a disposable cassette, or other dispenser, which will be connected to the tubing.

The shuttle is now translated 96 in the opposite direction, away from the cassette, removing the tubing cap, which is held in a pocket of the rotating finger. The finger is now rotated 97 away from the cassette, removing the port cap. The rotation may continue until the top of the rotating finger is below horizontal, and causing the caps atop the rotating finger to fall away. In one embodiment, the rotating finger includes an ejector plate that is actuated by a cam surface on the back wall of the autoconnect frame. After removal of the caps, the shuttle is translated forward 98, piercing the tubing seal with spikes in the cassette port. It is understood that this process is applicable to tubing from containers of a number of other liquid products, and may be used for automatically connecting to dispensers or pumping stations for the products.

Alternative Mechanisms for Shuttle Translation

The above descriptions have used an electric motor and lead screws to translate the shuttle, i.e., to move the shuttle back and forth in the direction to and from the disposable cassette, or other pumping or dispensing mechanism. Many other techniques and equipment may be used, a few of which are described in FIGS. 19-21.

Figure 19:
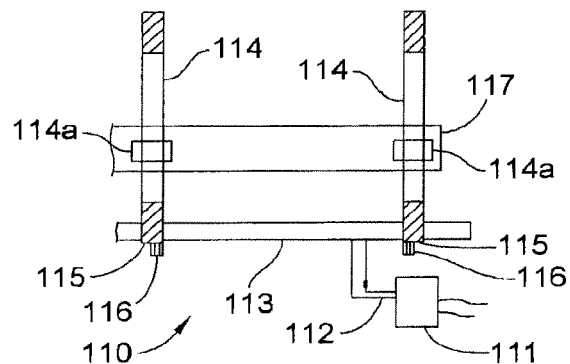
FIGS. 19-21 disclose alternative mechanical equipment for operating an autoconnect device.

A ballscrew, with a rotating nut and traveling balls, may also be used to translate the shuttle back and forth. FIG. 19 schematically depicts the use of ball screws in shuttle transport system 110. The shuttle transport system includes an electric motor 111 and its controller, suitable power transmission elements 112, and a power divider 113, to split power from the motor and drive two ballscrews 114. Each ballscrew is driven by a suitable interface 115 from power divider 113. Each ballscrew may also include an encoder 116 for sensing the shaft or ballscrew rotation, and thus the position of the shuttle 117. The shuttle 117 is mounted to the rotating nuts 114a of the ballscrews 117. As the ballscrews are rotated, the nuts translate or move back and forth, as does the shuttle. Other sensors may be used to determine shuttle position.

Figure 20:
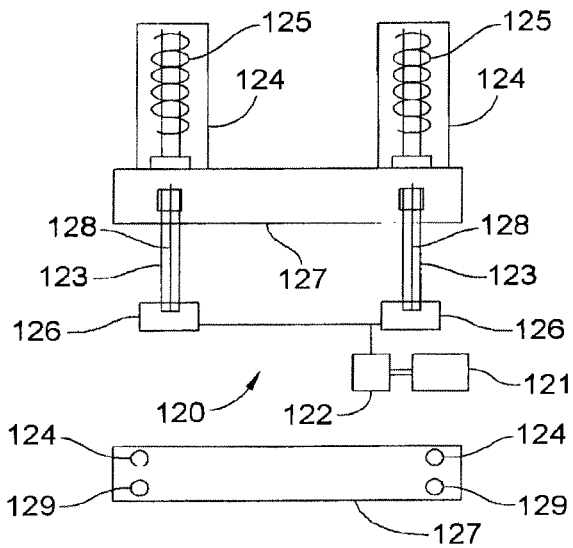

Pneumatic cylinders may also be used to move the shuttle back and forth, as shown in FIG. 20, depicting pneumatic shuttle transport system 120. Air may be supplied from a building compressor or plant air. For home use, however, a small air pump 121 and a suitable pressure regulator 122 and controller may be used. In this embodiment, shuttle 127 is mounted on the traveling or rod portions 124 of air cylinders 123. The cylinders may be single acting with an internal return spring 125 within the cylinder, or may be double-acting cylinders, for which no return spring is necessary. Air cylinders 123 are mounted on mounts 126, mounted on the autoconnect frame, for steady motion. The pneumatic driving system also includes a linear position sensor including linear transducers 128 mounted to the shuttle and the frame and sending out signals to the system controller of the position of the shuttle. As seen in the lower view of FIG. 20, the pneumatic system may include the pneumatic motive system as described, with shuttle 127 moved by air cylinder rods 124. Mounting rods or sliders 129 may also be used in parallel with the air cylinders.

Figure 21:
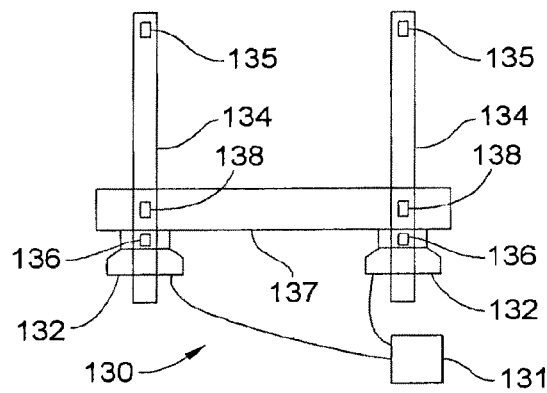

Because of the relatively short distances involved in translating the shuttle, it is also appropriate to use solenoids, preferably electric actuated, to translate the shuttle. FIG. 21 depicts an application in which solenoids are used in a solenoid transport system 130. Of course, more than one solenoid may be used, but solenoids with more than one position change are now available, such as the multi-position models from Guardian Electric Mfg. Co., Woodstock, Ill., U.S.A. In this application, shuttle 137 is mounted on the plungers 136 of solenoids 132. The solenoids are powered and controlled by controller 131. In addition, the position of the shuttle is noted by at least one hall effect sensor 138 on the shuttle and magnets 135 mounted at appropriate locations along the path of the shuttle. Other position sensors may also be used. In addition, the shuttle may use sliders 134, above or below the plane of the plungers, for travel in addition to the plungers of the solenoids mentioned above for the pneumatic shuttle transport system.

In addition, other mechanical or fluid power devices may be used for shuttle transport, such as hydraulics. Hydraulics are typically not used for medical devices because of certain aspects of hydraulic fluid. However, the autoconnect device uses relatively low power, and non-toxic hydraulic fluids are now available, such as the UCON™ FDC 300 and 400 grades from Dow Chemical. These fluids are approved for incidental food contact and may be safely used. A hydraulic system for shuttle transport would include at least a motor, a hydraulic pump, a reservoir for the hydraulic fluid, and control lines and systems for two-way movement of the shuttle.

Figure 22:
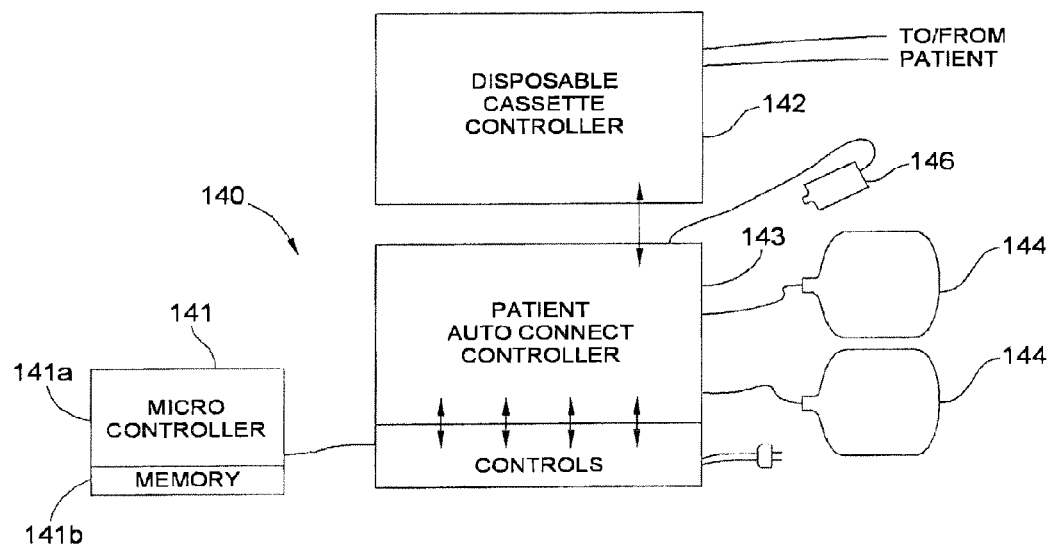
FIGS. 22-23 are schematic diagrams for a control system for operating an autoconnect machine, a pumping cassette, and a dialysis machine.
Figure 23:
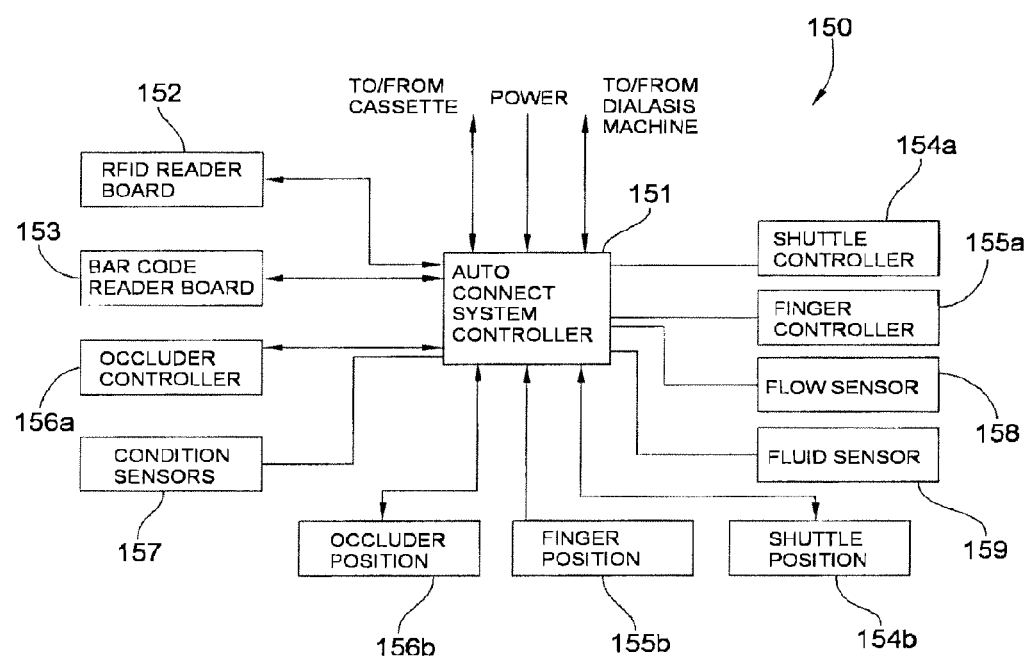

The control systems for operating the autoconnect and the associated equipment are also disclosed in FIGS. 22 and 23. The control system 140 for the dialysis machine, the disposable cassette, and the autoconnect device are depicted in FIG. 22. The patient autoconnect controller 143 is in communication with the disposable cassette controller 142 with an external interface. The autoconnect controller 143 is in communication with the dialysis machine controller 141 via an external patient autoconnect interface. Dialysis machine controller 141 includes a microcontroller 141a and a memory 141b for storing a computer program for operating the controller 141. The individual containers or bags of dialysis solution 144 are supplied with unique identifiers and when these identifiers are read, the containers may be said to interface with the dialysis machine controller 141, the disposable cassette controller 142, or as noted above, the autoconnect controller 143. The system controllers may also have other interfaces and connections. As noted above, the unique identifiers may be read in many ways, for example, by a camera 145 operably connected to the dialysis machine controller.

The term camera as used here also includes related optical devices capable of reading such a mark, including but not limited to, a visible/IR camera, a charge-coupled device (CCD), a CMOS image sensor or camera, an optical sensor, or other suitable device. Cameras for imaging in visible light are readily available. Cameras that capture infrared (heat) images are also available. Recently, cameras that can produce composite images using visible and infrared radiation are now available, such as those from Fluke Thermography and Fluke Corp., Everett, Wash., USA. Images that include an indication of temperature may also assist in the sense of letting users know when and if the containers have been warmed, for instance to body temperature. The camera may also be used to verify that the connectors are undamaged and that they are correctly loaded into the shuttle or other portion of the autoconnect device. If the connectors are damaged or the markings are inconsistent with the expected markings for the containers, the machine controller for the dialysis system or for the autoconnect device may signal an alarm or refuse to proceed. In one embodiment, the camera may also be used to inspect the color or other readily-determined optical property of the contents of the containers, and if the inspection of the color or other property does not yield the expected result, the system may signal an alarm or refuse to proceed.

The autoconnect control system 150 is depicted in FIG. 23. The autoconnect system is controlled by a microcontroller 151. A great many microcontrollers, and microprocessor controllers, are suitable for this application. Indeed, even application specific integrated controllers (ASICs) may be used. We have found that microcontrollers from STMicroelectronics, Austin, Tex., work well. Other microcontrollers that will be satisfactory include those from Freescale Corp., Austin, Tex., or Atmel Corp., San Jose, Calif. Other suitable microcontrollers may also be used.

System controller 151 is in communication with a great many other devices and parts of the autoconnect system, as discussed above. System controller 151 is in communication with RFID reader board 152, bar code reader board 153, if supplied, shuttle controller 154a, shuttle position sensor 154b, finger controller 155a, and finger position sensors 155b. In addition, the system controller 151 is in communication and control with the occluder controller 156a and the occluder position sensors 156b. In some systems, only a single occluder is used.

In addition, a number of additional sensors 157 are used in embodiments of the autoconnect system. For example, temperature sensors may be used near the tubing or the shuttle channels to detect a temperature related to the dialysis fluid or other liquid that is being auto-connected. Temperature sensors may also be used near the shuttle lead screws or other transport to insure that overheating is not occurring. If pneumatic cylinders or air solenoids are used, at least one or two pressure sensors should be used to keep a check on the health of the inlet air or air pump outlet that is used to supply air pressure. If hydraulic fluid is used, pressure sensors should be used to monitor and regulate hydraulic fluid pressure in the system.

It is also desirable to include a flow sensor 158. For example, a non-contacting optical flow sensor may be used to detect flow of dialysis fluid within the tubing, based on minute changes in reflection or refraction of the fluid within the tubing. A single pressure sensor of a two-port delta-p pressure sensor may be used along the tubing to detect flow by the change in pressure, or pressure drop, between the ports. Actual rotating, contact-type flow sensors may also be used. Finally, it may also be prudent to add a fluid sensor 159 for measuring specific properties of the solution, such as pH or conductivity. The fluid sensor is preferably placed directly in the flow stream for accurate measurement of the appropriate property.

Figure 24:
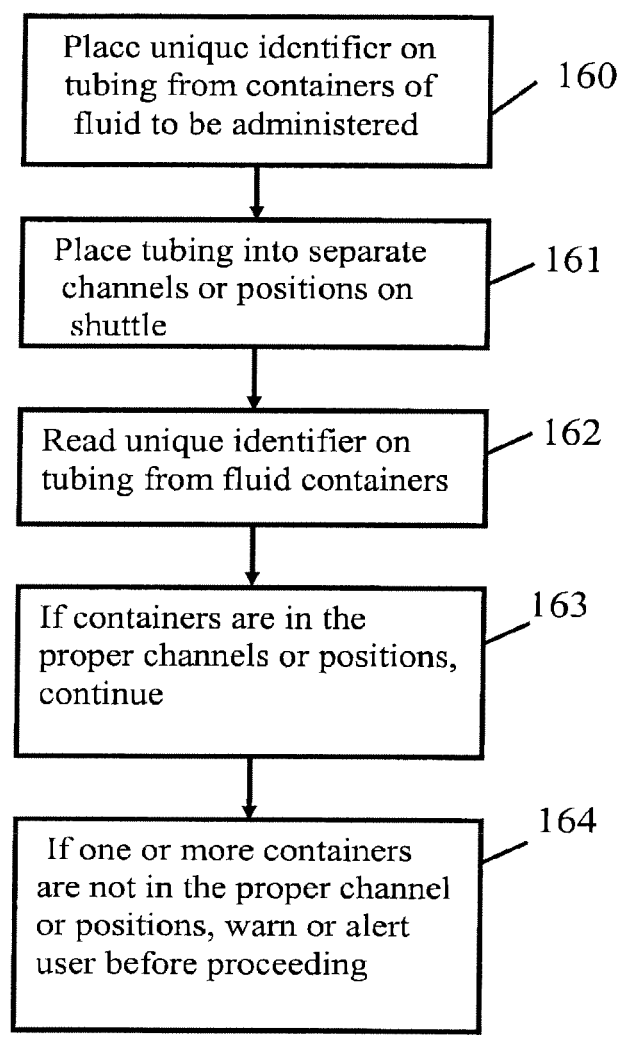
FIGS. 24-25 are flowcharts for methods of operating autoconnect devices.
Figure 25:
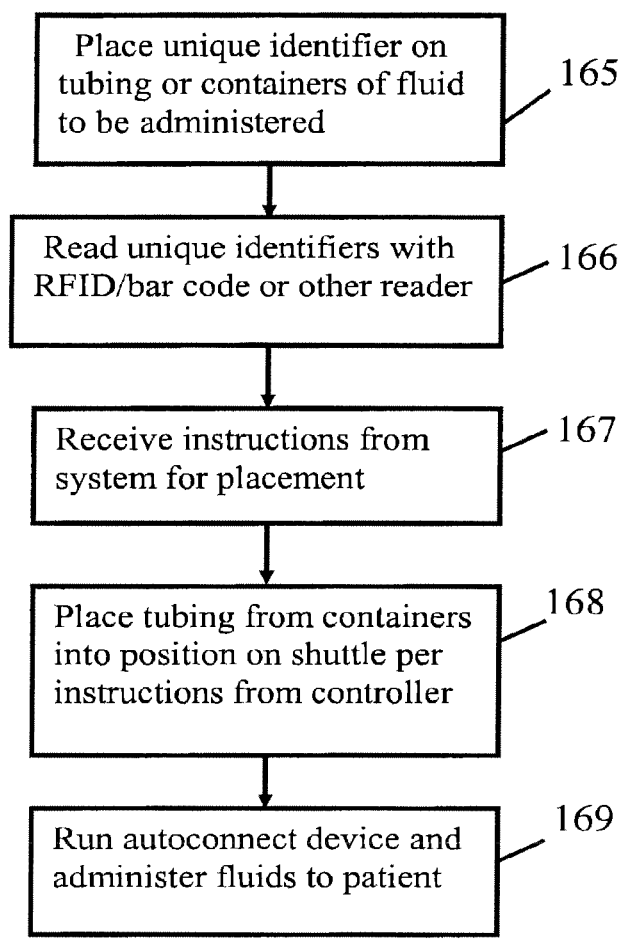

FIGS. 24-25 are flowcharts depicting how the automatic identification features of the autoconnect device operate in different embodiments. In one embodiment, depicted in FIG. 24, there is an RFID reader in each channel or position on the shuttle. There is also an RFID tag on the tubing from each container of fluid, such as dialysate fluid. The user places 160 an RFID tag with a unique identifier on tubing from the fluid container that contains the fluid to be administered to a patient. The tubing and RFID tag is then placed 161 into separate channels or positions on the shuttle. The reader in each position then reads 162 the RFID tag on the tubing from one or more containers. If the computer recognizes that the RFID tags corresponding to the containers are in the proper place, the operation continues 163. If one or more containers are not in the proper position, an alert or alarm is issued 164 to the user before proceeding.

In another embodiment, depicted in FIG. 25, there is only a single RFID reader or bar code reader operably connected to the autoconnect device. In this embodiment, the unique identifier for each container of fluid may be located 165 on tubing or on the container or bag itself. The user, using the bar code reader or RFID reader, then reads 166 the unique identifiers on each container or tubing, the unique identifiers being an RFID chip or bar code indicia or label. The computer and computer program receives the information about the containers and then instructs 167 the user concerning the position to place the tubing for each of the containers. The user then places 168 the tubing from the containers into the instructed position on the shuttle in accordance with the instructions. The user then operates 169 the autoconnect device and administers fluids to the patient.

It should be understood that various changes and modifications to the presently preferred embodiments described herein will be apparent to those having skill in the art. For instance, the autoconnect machine may be used with pumping cassettes used in peritoneal dialysis machines. Embodiments of autoconnect machines may also be used for cassettes for hemodialysis systems, automated peritoneal dialysis, and continuous flow peritoneal dialysis systems. These cassettes may employ any suitable pump or other fluid transfer mechanism, used with the autoconnect machine. Such changes and modifications can be made without departing from the spirit and scope of the present disclosure and without diminishing its intended advantages. Such changes and modifications are included in the appended claims.

What is claimed is:

1. A medical fluid system with supply autoconnection, the medical fluid system comprising:
    at least two fluid containers and a tube extending from each of the two containers, wherein each of the tubes includes a cap on a tube end;
    a fluid pumping cassette including at least two port spikes;
    a medical fluid machine including
        at least two occluders,
        a shuttle configured to receive the tubes, wherein each of the tubes is operably associated with one of the at least two occluders,
        a driving mechanism for translating the shuttle, and
        a cap removal device positionable between the fluid pumping cassette and the translating shuttle; and
    a control unit programmed to cause (i) the occluders to pinch their associated tubes to prevent fluid flow, (ii) the driving mechanism to translate the shuttle holding the occluded tubes towards the fluid pumping cassette, the cap removal device in turn engaging the tube caps, (iii) the driving mechanism to translate the shuttle holding the occluded tubes away from the fluid pumping cassette and the cap removal device, so that the cap removal device pulls the tube caps off of the tube ends of the respective tubes, and (iv) the driving mechanism to translate the shuttle back towards the fluid pumping cassette to allow the port spikes of the fluid pumping cassette to spike the tube ends of the occluded tubes.

2. The medical fluid system of claim 1, which includes a motor-driven lead screw coupled to the shuttle to translate the shuttle.

3. The medical fluid system of claim 1, wherein each of the tube ends includes a seal positioned and arranged to be spiked by one of the port spikes of the fluid pumping cassette.

4. The medical fluid system of claim 1, which includes a reader operable with the control unit, and wherein each of the tube ends includes an identifier tag positioned and arranged to be read by the reader.

5. The medical fluid system of claim 1, wherein the control unit is further programmed to move the cap removal device out from between the shuttle and the fluid pumping cassette so that in (iv) the shuttle can be translated back towards the fluid pumping cassette.

6. The medical fluid system of claim 5, wherein the shuttle and the cap removal device are separately motorized.

7. The medical fluid system of claim 1, which includes a spike cap fitted onto each of the port spikes of the fluid pumping cassette.

8. The medical fluid system of claim 7, wherein the control unit causes the cap removal device in (ii) to be moved by the shuttle to engage each spike cap and in (iii) to pull the spike caps off of each of the respective port spikes of the fluid pumping cassette.

9. The medical fluid system of claim 1, which also includes at least one sensor associated with the shuttle and operable with the control unit to provide shuttle position information to the controller.

10. The medical fluid system of claim 9, wherein the sensor is an optical sensor (a) sensing the moving shuttle or (b) moveable with the shuttle to sense stationary targets.

11. The medical fluid system of claim 9, wherein the sensor is a proximity sensor (a) sensing the moving shuttle or (b) moveable with the shuttle to sense stationary targets.

12. A medical fluid machine operable with a fluid pumping cassette having at least two port spikes, the fluid pumping cassette in fluid communication with at least two fluid containers, each container including a tube extending therefrom, wherein each tube includes a cap on a tube end, the medical fluid machine comprising:
    at least two occluders;
    a shuttle configured to receive the tubes extending from the at least two fluid containers, wherein each of the tubes is operably associated with one of the at least two occluders;
    a driving mechanism for translating the shuttle;
    a cap removal device positionable between the fluid pumping cassette and the translating shuttle; and
    a control unit programmed to cause (i) the occluders to pinch their associated tubes to prevent fluid flow, (ii) the driving mechanism to translate the shuttle holding the occluded tubes towards the fluid pumping cassette, the cap removal device in turn engaging the tube caps, (iii) the driving mechanism to translate the shuttle holding the occluded tubes away from the fluid pumping cassette and the cap removal device, so that the cap removal device pulls the tube caps off of the tube ends of the respective tubes, and (iv) the driving mechanism to translate the shuttle back towards the fluid pumping cassette to allow the port spikes of the fluid pumping cassette to spike the tube ends of the occluded tubes.

13. The medical fluid machine of claim 12, which includes a motor-driven lead screw coupled to the shuttle to translate the shuttle.

14. The medical fluid machine of claim 12, wherein the control unit is further programmed to move the cap removal device out from between the shuttle and the fluid pumping cassette so that in (iv) the shuttle can be translated back towards the fluid pumping cassette.

15. The medical fluid machine of claim 12, which also includes at least one sensor associated with the shuttle and operable with the control unit to provide to shuttle position information to the control unit.

16. The medical fluid machine of claim 15, wherein the sensor is an optical sensor (a) sensing the moving shuttle or (b) moveable with the shuttle to sense stationary targets.

17. The medical fluid machine of claim 15, wherein the sensor is a proximity sensor (a) sensing the moving shuttle or (b) moveable with the shuttle to sense stationary targets.

18. A method of connecting fluid containers to a fluid pumping cassette including a plurality of port spikes, the method comprising:
    mounting the fluid pumping cassette to a medical fluid machine;
    receiving tubes extending from the fluid containers and associating each tube with one of the plurality of port spikes, each tube including a tube cap on a tube end;
    occluding the tubes to prevent fluid flow;

translating the occluded tubes towards the fluid pumping cassette;

causing the medical fluid machine to engage each of the tube caps;

translating the occluded tubes away from the fluid pumping cassette to pull the tube caps off of the tube ends of the tubes; and translating the occluded tubes towards the fluid pumping cassette to allow the port spikes of the fluid pumping cassette to spike the tube ends of the occluded tubes.

19. The method of claim 18, which further includes reading identification tags on the tubing.

20. The method of claim 19, which includes moving the removed tube caps out of a path between the tube ends and the fluid pumping cassette to translate the occluded tubes towards the fluid pumping cassette to allow the port spikes of the fluid pumping cassette to spike the tube ends of the occluded tubes.

* * * * *